(12) United States Patent
Yoshimura et al.

(10) Patent No.: US 11,478,220 B2
(45) Date of Patent: Oct. 25, 2022

(54) ULTRASONIC TRANSMITTING AND RECEIVING ELEMENT, AND ULTRASONIC EXAMINATION DEVICE, SMARTPHONE, AND TABLET INCLUDING THE SAME

(71) Applicant: Hitachi, Ltd., Tokyo (JP)

(72) Inventors: Yasuhiro Yoshimura, Tokyo (JP); Akifumi Sako, Tokyo (JP); Masahiro Sato, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 645 days.

(21) Appl. No.: 16/359,020

(22) Filed: Mar. 20, 2019

(65) Prior Publication Data

US 2019/0321002 A1 Oct. 24, 2019

(30) Foreign Application Priority Data

Apr. 24, 2018 (JP) .............................. JP2018-083490

(51) Int. Cl.
*A61B 8/00* (2006.01)
*G01N 29/24* (2006.01)
*B06B 1/02* (2006.01)

(52) U.S. Cl.
CPC .............. *A61B 8/4444* (2013.01); *A61B 8/44* (2013.01); *A61B 8/4494* (2013.01); *G01N 29/2406* (2013.01); *A61B 8/4427* (2013.01); *B06B 1/0292* (2013.01)

(58) Field of Classification Search
CPC ....... A61B 8/4444; A61B 8/44; A61B 8/4494; A61B 8/4427; G01N 29/2406; B06B 1/0292; H05K 3/361–365; H05K 3/325–326; H05K 1/189
See application file for complete search history.

(56) References Cited

U.S. PATENT DOCUMENTS

| | | | |
|---|---|---|---|
| 8,540,640 B2 * | 9/2013 | Sano | G01N 29/0654 600/459 |
| 2006/0170112 A1 * | 8/2006 | Tanaka | H01L 24/05 257/777 |

(Continued)

FOREIGN PATENT DOCUMENTS

| | | |
|---|---|---|
| CN | 103298410 A | 9/2013 |
| JP | 2006-210745 A | 8/2006 |

(Continued)

OTHER PUBLICATIONS

Chinese-language Office Action issued in Chinese Application No. 201910219293.5 dated Jul. 28, 2021 with English translation (17 pages).

(Continued)

*Primary Examiner* — Sean D Mattson
(74) *Attorney, Agent, or Firm* — Crowell & Moring LLP

(57) ABSTRACT

According to one embodiment, an ultrasonic probe includes: an oscillator; a base on which the oscillator is provided; a base conductive wire portion connected to the oscillator; a bump electrode portion supplying a signal to the oscillator via the base conductive wire portion; a pad portion engaging with the bump electrode portion; and an acoustic lens provided such that a force toward the bump electrode portion is applied to the pad portion.

14 Claims, 15 Drawing Sheets

(56) References Cited

U.S. PATENT DOCUMENTS

| | | | |
|---|---|---|---|
| 2008/0257586 A1* | 10/2008 | Chen | H05K 1/0283 |
| | | | 29/829 |
| 2009/0061656 A1* | 3/2009 | Tanaka | H05K 3/368 |
| | | | 439/75 |
| 2009/0062655 A1* | 3/2009 | Saito | G10K 11/02 |
| | | | 600/459 |
| 2010/0013574 A1* | 1/2010 | Huang | B06B 1/0292 |
| | | | 333/186 |
| 2012/0245470 A1* | 9/2012 | Ooishi | A61B 8/4444 |
| | | | 600/459 |
| 2013/0226001 A1* | 8/2013 | Steen | G01S 7/5208 |
| | | | 600/447 |
| 2013/0285174 A1 | 10/2013 | Sako et al. | |
| 2015/0112201 A1* | 4/2015 | Nakanishi | A61B 8/4411 |
| | | | 600/472 |
| 2015/0290679 A1* | 10/2015 | Kandori | G10K 11/004 |
| | | | 367/7 |

FOREIGN PATENT DOCUMENTS

| | | | |
|---|---|---|---|
| JP | 2011255024 A | * | 12/2011 |
| JP | 2015-128270 A | | 7/2015 |

OTHER PUBLICATIONS

Chinese-language Office Action issued in Chinese Application No. 201910219293.5 dated Dec. 8, 2021 with English translation (15 pages).

Chinese-language Office Action issued in Chinese Application No. 201910219293.5 dated Apr. 18, 2022 with partial English translation (seven (7) pages).

* cited by examiner

ULTRASONIC TRANSMITTING AND RECEIVING ELEMENT, AND ULTRASONIC EXAMINATION DEVICE, SMARTPHONE, AND TABLET INCLUDING THE SAME

BACKGROUND OF THE INVENTION

1. Field of the Invention

The present invention relates to an ultrasonic transmitting and receiving element, an ultrasonic examination device, and a smartphone and a tablet which include the ultrasonic transmitting and receiving element.

2. Description of Related Art

In the related art, as needs for ultrasonic sensors, for example, there is a tactile sensor or a touch sensor that simulates human hands, an ultrasonic flaw detector that detects an internal defect of a structural material and a probe for an ultrasonic examination device used for a medical examination of people or animals.

An ultrasonic sensing device is provided with a wiring for sending an ultrasonic transmission signal transmitted from an ultrasonic element and a reception signal received by an ultrasonic element to a signal processing circuit and the like outside the ultrasonic element.

As an ultrasonic sensor using a semiconductor substrate, there are a piezoelectric micro-machined ultrasonic transducer (PMUT) using a piezoelectric element and a capacitive micro-machined ultrasonic transducer (CMUT) of a capacitive ultrasonic transducer applying a semiconductor technology. Both the PMUT and the CMUT are devices that generate ultrasonic waves by vibrating a diaphragm, but are different from each other in driving systems.

The PMUT is driven by a piezoelectric element having a piezoelectric effect. The CMUT is driven by a capacitive system that drives an electrode film with an electrostatic force applied to electrodes installed in parallel via space. Although driving force generation systems are different in the PMUT and the CMUT, wiring connected for transmitting and receiving signals by driving the diaphragm is from an ultrasonic transmitting and receiving surface or a back surface of an element.

As a wiring system to be connected to the outside from the ultrasonic transmitting and receiving surface, there is a method in which an electrode pad of a flexible substrate arranged adjacent to the element and an electrode pad of the element are connected to each other by wire bonding. Also, there is a method in which the electrode pad of the element and the electrode pad of the flexible substrate are caused to face so as to be bonded to each other. In a case of drawing the wiring to be connected to the outside from the back surface, there is provided a structure in which a through electrode penetrating the substrate having the element formed thereon is formed and the through electrode is connected to a flexible substrate or the like.

JP-A-2015-128270 (FIG. 2, paragraph 0021, FIG. 6-1, paragraph 0041, and the like) refers to drawing out a wiring of a capacitive transducer.

A second embodiment of JP-A-2015-128270 (FIG. 2, paragraph 0021, FIG. 6-1, paragraph 0041, and the like) describes as follows. "An electrode on a chip and an electrode part where a wiring layer of a flexible wiring substrate is exposed are arranged so as to face each other. A bump is formed in a portion where the wiring layer of the flexible wiring substrate is exposed to be electrically connected to the electrode on the chip. As the bump, a solder bump, a gold bump, and the like can be used. The connection between the bump and the electrode can be easily realized by using flip chip mounting technology used for semiconductor mounting."

Furthermore, a sixth embodiment describes as follows. "When an acoustic lens is pressed against the chip and attached thereto, the acoustic lens can be widely supported at a CMUT or a surface having no electrode (particularly, at four corners of the chip). Therefore, thinning of a bonding layer or occurrence of deformation of the lens itself can be reduced. Therefore, it becomes easy to attach the acoustic lens so as to be parallel to a CMUT disposing surface, and the deformation of the acoustic lens or the thickness unevenness of the bonding layer can be reduced."

As described above, JP-A-2015-128270 (FIG. 2, paragraph 0021, FIG. 6-1, paragraph 0041, and the like) discloses a technology relating to a structure of a wiring drawing portion of the capacitive transducer.

Also, JP-A-2006-210745 (FIG. 1, Abstract, and the like) refers to a structure of a wiring connecting portion between semiconductor chips.

In the Abstract of JP-A-2006-210745 (FIG. 1, Abstract, and the like), [Object] discloses a method capable of three-dimensionally connecting a plurality of different semiconductor chips one another with the shortest wiring length using a penetrating electrode and high-speed operating with low noise. [Solving Means] discloses "In a three-dimensional chip stacked structure obtained by disposing an interposer chip, that connects upper and lower chips to each other, in the middle of different upper and lower semiconductor chips, a hole reaching a surface electrode is formed at the back surface position corresponding to an external electrode portion on a device side (surface layer side) by dry etching, a metal plating film is applied to a side wall and a periphery on the back surface side of the hole, a metallic bump of another semiconductor chip stacked on an upper side is deformed and injected by pressure welding into an inside of the through electrode to which the metal plating film has been applied, and the metal bump is geometrically caulked and electrically connected to the inside of the through electrode formed in the semiconductor chip."

That is, JP-A-2006-210745 (FIG. 1, Abstract, and the like) describes a method of electrical connection between semiconductor chips.

However, the technology described in JP-A-2015-128270 (FIG. 2, paragraph 0021, FIG. 6-1, paragraph 0041, and the like) has the following problems.

In the method of connection between the electrode on the chip of the capacitive transducer and the flexible wiring substrate described in JP-A-2015-128270 (FIG. 2, paragraph 0021, FIG. 6-1, paragraph 0041, and the like), the connection to the flexible wiring substrate is made via a bump formed on the electrode on the chip. However, for the connection, it is required to perform heating. In a case of a solder bump, it is required to perform heating at around 200° C.

On the other hand, since the chip is mounted on a backing material and is required to have a function to attenuate unnecessary ultrasonic waves emitted toward the back surface side of a chip, as a function of the backing material, a resin composite material or the like is used therefor. Since a heat resistant temperature of the resin composite material is, for example, approximately 200° C., there is a problem of lowering the temperature for bonding by the solder bump. Furthermore, in a case where the bonding temperature is lowered, there are problems that bonding strength is low, electrical connection resistance also increases, and connection reliability decreases.

Furthermore, it is described that the acoustic lens is pressed against a chip and attached thereto. However, there is no description regarding lifting or the like of the flexible substrate when pressed, such as a structure of an attaching portion of the acoustic lens.

Also, the technology described in JP-A-2006-210745 (FIG. 1, Abstract, and the like) has the following problems.

In a method of laminating semiconductor chips described in JP-A-2006-210745 (FIG. 1, Abstract, and the like), a through hole is formed in the chip, a metal plating is applied to the hole, and a chip on which the metal bump is formed is geometrically caulked and electrically connected to the hole to which the metal plating has been applied. However, a material of the semiconductor chip is silicon of a brittle material. Therefore, when a pressing force required for caulking is high, there is a concern that cracking may occur in the chip in which the hole is formed, and there is a problem that reliability decreases.

SUMMARY OF THE INVENTION

The present invention has been made in view of the above circumstances, and an object thereof is to provide an ultrasonic transmitting and receiving element in which lifting of a substrate and cracking at the time of connection are suppressed to enhance mechanical and electrical connection reliability, an ultrasonic examination device, and a smartphone and a tablet which include the ultrasonic transmitting and receiving element.

In order to solve the problems, an ultrasonic probe according to an first aspect of the present invention includes: an oscillator; a base on which the oscillator is provided; a base conductive wire portion connected to the oscillator; a bump electrode portion supplying a signal to the oscillator via the base conductive wire portion; a pad portion engaging with the bump electrode portion; and an acoustic lens provided such that a force toward the bump electrode portion is applied to the pad portion.

An ultrasonic probe according to a second aspect of the present invention includes: an acoustic lens; an oscillator; a base on which the oscillator is provided; a base conductive wire portion connected to the oscillator; a bump electrode portion supplying a signal to the oscillator via the base conductive wire portion; and a pad portion to which the bump electrode portion is press-fitted.

An ultrasonic probe according to a third aspect of the present invention includes: an acoustic lens; an oscillator; a base on which the oscillator is provided; a base conductive wire portion connected to the oscillator; a bump electrode portion supplying a signal to the oscillator via the base conductive wire portion; a pad portion facing the bump electrode portion and connected thereto; and a flexible substrate on which the pad portion or the bump electrode portion is provided.

An ultrasonic examination device according to a fourth aspect of the present invention having a transmitting function of ultrasonic waves and a receiving function of ultrasonic waves reflected from an object, includes: an image forming unit converting a received signal obtained from the receiving function into an image; a display unit displaying the image; and the ultrasonic probe according to any one of the first, second, or fourth aspect of the present invention.

A smartphone according to a fifth aspect of the present invention having a transmitting function of ultrasonic waves and a receiving function of ultrasonic waves reflected from an object, the device includes: an image forming unit converting a received signal obtained from the receiving function into an image; a display unit displaying the image; and the ultrasonic probe according to any one of the first, second, or fourth aspect of the present invention.

A tablet according to a sixth aspect of the present invention having a transmitting function of ultrasonic waves and a receiving function of ultrasonic waves reflected from an object, the device includes: an image forming unit converting a received signal obtained from the receiving function into an image; a display unit displaying the image; and the ultrasonic probe according to any one of the first, second, or fourth aspect of the present invention.

According to the present invention, it is possible to provide an ultrasonic transmitting and receiving element in which lifting of a substrate and cracking at the time of connection are suppressed to enhance mechanical and electrical connection reliability, an ultrasonic examination device, and a smartphone and a tablet which include the ultrasonic transmitting and receiving element.

DESCRIPTION OF EMBODIMENTS

Hereinafter, embodiments of the present invention will be described in detail, with reference to drawings as appropriate.

The present invention relates to an ultrasonic transmitting and receiving element and a measuring device using the same, and particularly to an ultrasonic probe that captures an examination image and an ultrasonic examination device using the same.

Figure 1:
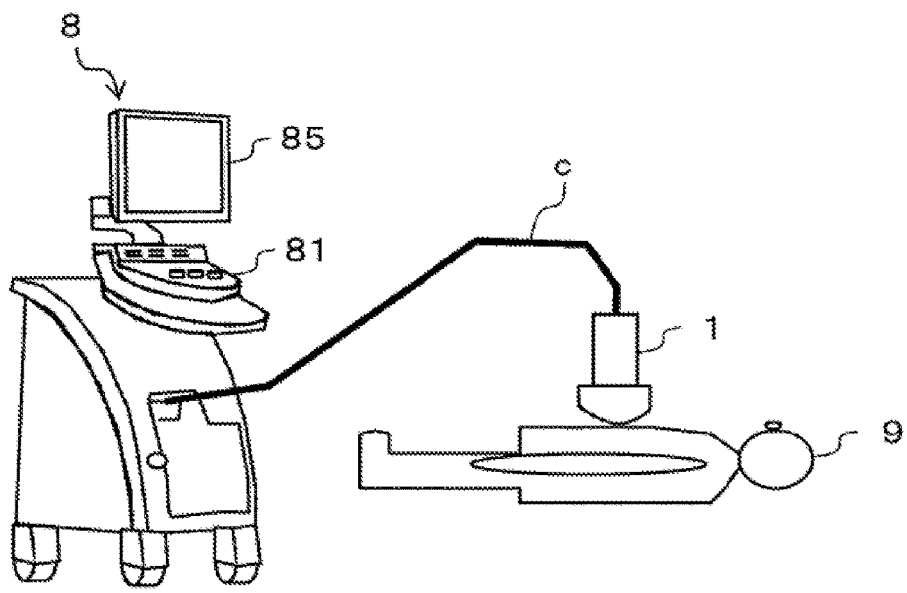
FIG. 1 is a schematic external diagram illustrating a using state of an ultrasonic probe and an ultrasonic examination device according to an embodiment of the present invention.

FIG. 1 illustrates a specific application example of the present invention.

FIG. 1 is a schematic external diagram illustrating a using state of an ultrasonic probe 1 and an ultrasonic examination device 8, according to an embodiment of the present invention. FIG. 1 illustrates an aspect in which an object 9 is ultrasonically examined with the ultrasonic probe 1.

The ultrasonic probe 1 of the embodiment is connected to the ultrasonic examination device 8 that performs control and analysis for an ultrasonic examination.

When performing the ultrasonic examination, first, an operator (not illustrated) inputs an examination condition relating to the object 9 using a control panel 81. Then, the operator performs the examination by scanning a body surface in the vicinity of a subject to be examined of the object 9 with the ultrasonic probe 1.

The ultrasonic probe 1 is electrically connected to the ultrasonic examination device 8 via a cable c or the like. The ultrasonic probe 1 receives a control signal from the ultrasonic examination device 8 and transmits an ultrasonic signal to the object 9. In this case, the ultrasonic probe 1 receives the ultrasonic signal reflected as an echo from the object 9. The received ultrasonic signal (received signal) is transmitted to the ultrasonic examination device 8 by the ultrasonic probe 1. The received ultrasonic signal is converted into an ultrasonic image by the ultrasonic examination device 8 and displayed on a display unit 85.

In this manner, the operator can examine an inside of the object 9 by visualizing.

Figure 2:
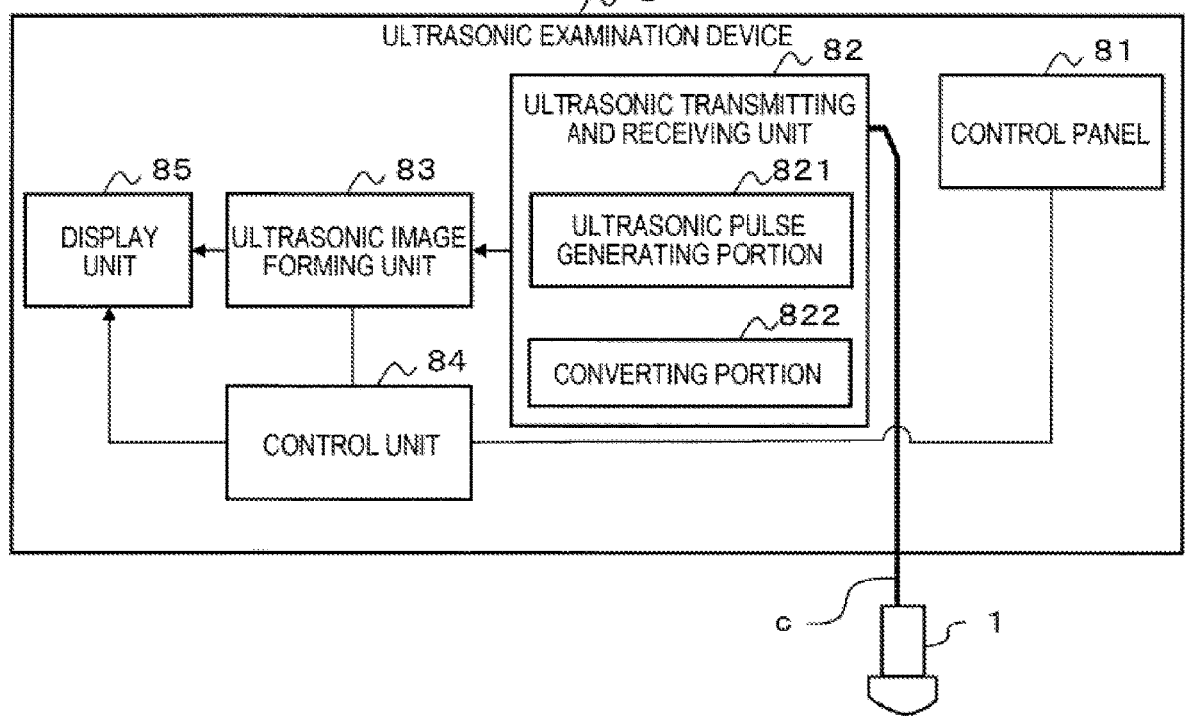
FIG. 2 is a block diagram illustrating a configuration of an ultrasonic probe and an ultrasonic examination device according to an embodiment.

FIG. 2 is a block diagram illustrating a configuration of the ultrasonic probe 1 and the ultrasonic examination device 8 according to an embodiment.

The ultrasonic examination device 8 creates a two-dimensional ultrasonic image, a three-dimensional ultrasonic image, various Doppler images, or the like of a site to be examined of the subject to be examined, by using the echo signal obtained by the ultrasonic probe 1 transmitting the ultrasonic waves to an inside of the object 9, to display the image.

Therefore, the ultrasonic examination device 8 is configured to include an ultrasonic transmitting and receiving unit 82, an ultrasonic image forming unit 83, a control unit 84, the display unit 85, and the control panel 81.

An ultrasonic probe 1 is electrically connected to the ultrasonic transmitting and receiving unit 82. The ultrasonic transmitting and receiving unit 82 transmits a control signal to the ultrasonic probe 1 and receives an electric signal by the echo from the ultrasonic probe 1.

The ultrasonic probe 1 plays a role in transmitting the ultrasonic waves to the object 9 and receiving the reflected echo.

Figure 3:
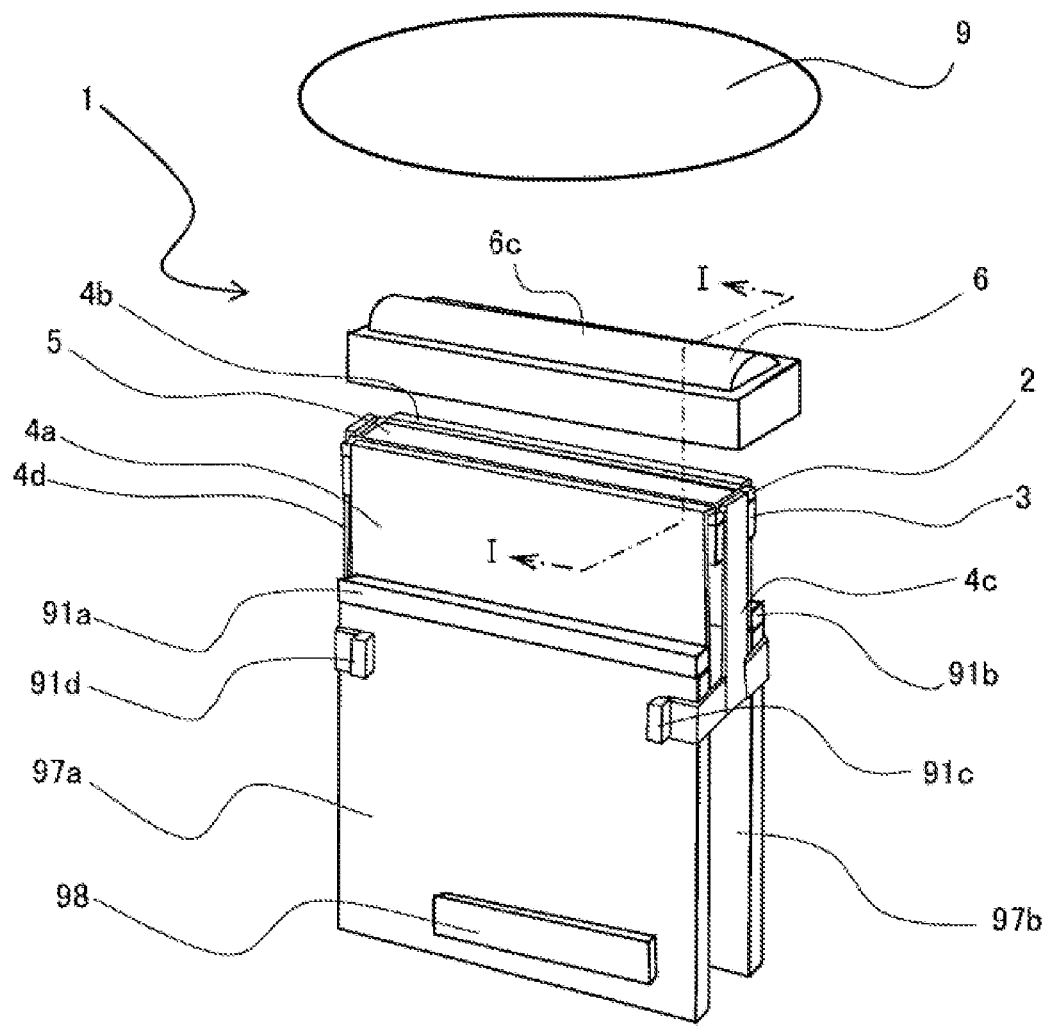
FIG. 3 is an exploded perspective diagram illustrating a schematic configuration of an ultrasonic probe.
Figure 4:
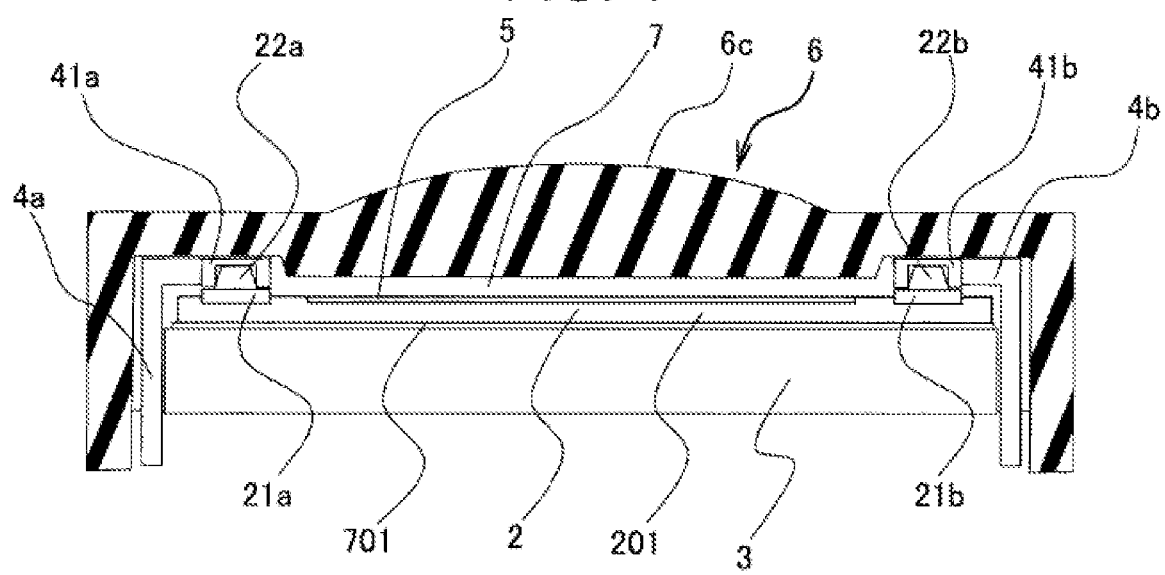
FIG. 4 is a schematic diagram illustrating a partial section taken along the line I-I of the ultrasonic probe illustrated in FIG. 3 according to a first embodiment.

A CMUT chip 2 is installed in the ultrasonic probe 1 (see FIGS. 3 and 4). The CMUT chip 2 is an ultrasonic transmitting and receiving device prepared by laminating thin films, by applying a semiconductor manufacturing technology and a micro electro mechanical system (MEMS) technology.

The ultrasonic transmitting and receiving unit 82 generates a pulsed electric signal for generating an ultrasonic signal to be transmitted to the object 9 by the ultrasonic probe 1. The ultrasonic transmitting and receiving unit 82 includes an ultrasonic pulse generating portion 821 that transmits the generated electric signal to the ultrasonic probe 1 and a converting portion 822 that converts the echo signal received by the ultrasonic probe 1 into an electric signal. The ultrasonic transmitting and receiving unit 82 may be, for example, any of commercially available ultrasonic transceiver.

The ultrasonic image forming unit 83 forms the two-dimensional ultrasonic image, a three-dimensional ultrasonic image, various Doppler images, or the like, from the electric signal converted from the echo signal. Specifically, the ultrasonic image forming unit 83 is configured of, for example, a central processing unit (CPU), a microcomputer, and the like.

The display unit 85 displays the ultrasonic image formed by the ultrasonic image forming unit 83. Also, information input by the control panel 81 and other information necessary for the examination are displayed together on the display unit 85. Specifically, the display unit 85 is configured of, for example, a liquid crystal density (LCD), a microcomputer, and the like.

The control unit 84 controls each unit (1, 81, 82, 83, 85, and the like) based on the control information input by the control panel 81. Specifically, the control unit 84 is configured of, for example, a CPU, a microcomputer, and the like.

The control panel 81 receives an input of certain information by the operator such that the operator can perform a desired examination on the object 9. The control unit 84 controls each unit (such as 1, 81, 82, 83, and 85), based on the information input to the control panel 81. Specifically, the control panel 81 is configured of, for example, a push button, a touch panel for sensing a change in electrostatic capacity, and the like.

FIG. 3 is an exploded perspective diagram illustrating a schematic configuration of the ultrasonic probe 1.

The ultrasonic probe 1 includes the CMUT chip 2 on one side of a backing material 3 of a support material. The CMUT chip 2 includes an acoustic lens 6 made of silicone rubber for focusing the ultrasonic waves generated from the CMUT chip 2 in a direction of the object 9, on a surface thereof (see FIG. 1).

The CMUT chip 2 transmits and receives the ultrasonic waves to and from the object 9 through the acoustic lens 6. That is, the CMUT chip 2 irradiates the subject to be examined of the object 9 with the ultrasonic waves through the acoustic lens 6. Then, the CMUT chip 2 receives the ultrasonic waves reflected from the subject to be examined of the object 9.

The CMUT chip 2 is electrically connected to flexible substrates 4a, 4b, 4c, and 4d having a wiring of a conductive wire member connected to connectors 91a, 91b, 91c, and 91d. The connectors 91a, 91b, 91c, and 91d are connected to circuit boards 97a and 97b. Although not illustrated, the connectors are also in a back side position of FIG. 3, opposite the connectors 91c and 91d. Accordingly, the CMUT chip 2, the flexible substrates 4a, 4b, 4c, and 4d, and the circuit boards 97a and 97b are connected to one another.

A connection terminal 98 disposed on the circuit board 97a is connected to the ultrasonic examination device 8 (see FIG. 2) via the cable c.

In the CMUT chip 2, an element portion 5 that transmits and receives ultrasonic waves is formed.

In this regards, the ultrasonic examination device 8 (see FIG. 2) is a device applying an electric signal to the CMUT chip 2 to vibrate a diaphragm (not illustrated) of the element portion 5 and to make the signal received by waves from the object 9 form an image. Here, the diaphragm is a film in which displacement occurs in accordance with an action of the electrostatic force.

First Embodiment

FIG. 4 is a schematic diagram illustrating a partial section taken along the line I-I of the ultrasonic probe 1 illustrated in FIG. 3, according to a first embodiment.

The CMUT chip 2 is attached and fixed to an upper surface of the backing material 3 of the supporting material via a bonding film 701. In the CMUT chip 2, an element portion 5 that transmits and receives ultrasonic waves is integrally formed on a surface using a silicone plate 201 as a base.

Pads 21a and 21b for electrical connection are formed on outer sides of the element portion 5 of the CMUT chip 2. Although not illustrated, a membrane electrode of a diaphragm-like (displacement generating film) and a fixed electrode facing the membrane electrode via space which are formed in the element portion 5 are connected to the pads 21a and 21b by wiring with a conductive material. Convex bumps 22a and 22b are respectively formed on the pads 21a and 21b to configure bump electrodes together with the pads 21a and 21b.

Holed-pads 41a and 41b are respectively formed in the flexible substrates 4a and 4b respectively corresponding to the bump electrodes (21a, 22a and 21b, 22b) of the CMUT chip 2. The holed-pads 41a and 41b of the flexible substrates 4a and 4b are respectively engaged with the bumps 22a and 22b, and are electrically and mechanically connected thereto. Although not illustrated, the wiring formed of the conductive material formed on the flexible substrates 4a and 4b and the holed-pads 41a and 41b are connected to each other.

According to this configuration, signals transmitted and received from the element portion 5 are sent to the circuit boards 97a, 97b (see FIG. 3) through the conductive material formed on the CMUT chip 2, the pads 21a and 21b and the bumps 22a and 22b of the CMUT chip 2, the holed-pads 41a and 41b of the flexible substrates 4a and 4b, and the conductive material formed on the flexible substrates 4a to 4d.

Here, the element portion 5 will be described in detail.

In the element portion 5, a plurality of diaphragms (diaphragm-like membrane electrodes) are arranged adjacent to each other in an array to form a unit. A plurality of units are further arranged to form the element portion 5. Several units are combined and electrodes are connected to configure one channel.

As illustrated in FIG. 4, the acoustic lens 6 is attached and fixed using an adhesive 7 to an upper part of an assembly in which the CMUT chip 2 and the flexible substrates 4a and 4b are mounted on the backing material 3. The adhesive 7 may be a silicone resin having an acoustic impedance equal to that of the acoustic lens 6 and hardness to extent that vibration of the diaphragm-like membrane electrode is not hindered. A thickness of the adhesive 7 may be 50 μm or less in consideration of the influence of a transfer characteristic of the ultrasonic waves, and more preferably, 20 μm or less.

Figure 5A:
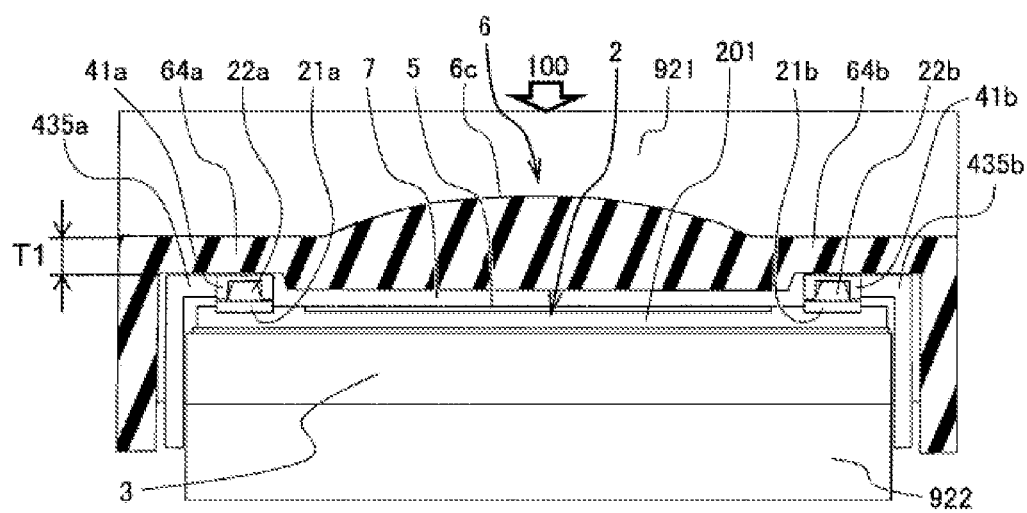
FIG. 5A is a sectional diagram of a main part illustrating a state when bonding an acoustic lens according to another example according to the first embodiment.
Figure 5B:
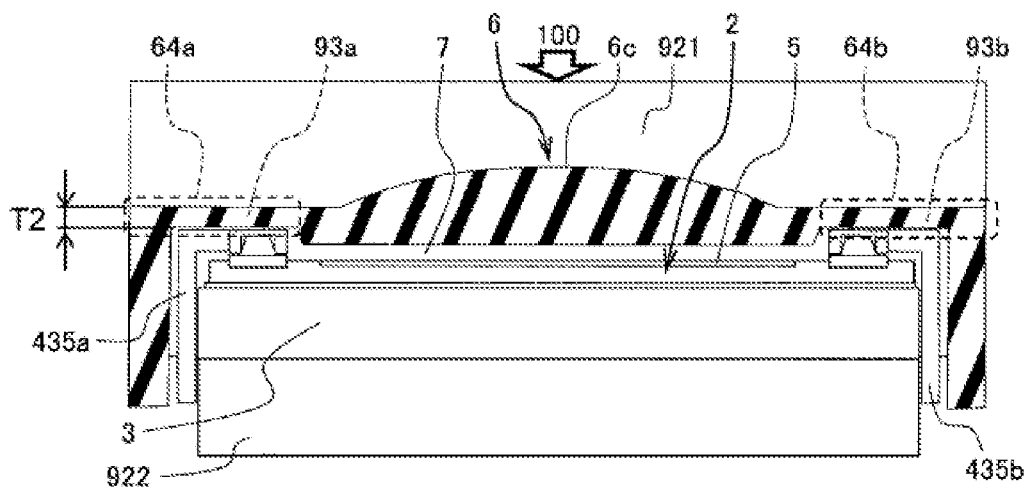
FIG. 5B is a sectional diagram illustrating a state in which a load is applied by a pressure tool according to still another example according to the first embodiment.
Figure 5C:
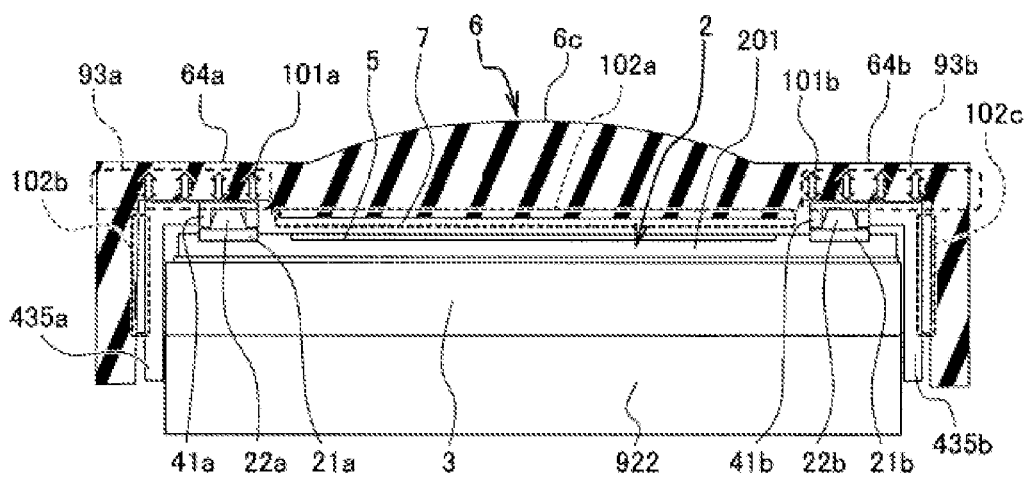
FIG. 5C is a diagram illustrating an example of an installation status of an acoustic lens according to still another example according to the first embodiment.

FIGS. 5A to 5C are diagrams illustrating examples of an installation status of the acoustic lens according to another example of the first embodiment.

FIG. 5A is a sectional diagram of a main part illustrating a state when bonding the acoustic lens 6.

The acoustic lens 6 has a curved surface portion 6c at the center portion and arm portions 62a and 62b on a periphery of the curved surface portion 6c. The arm portions 62a and 62b cover flexible substrates 435a and 435b from the outer sides, respectively.

Installation of the acoustic lens 6 is performed as follows.

A base 922 is installed under the backing material 3. After the CMUT chip 2 having the element portion 5 is coated with the adhesive 7, the acoustic lens 6 is placed and a pressure tool 921 is installed thereon. Then, a load 100 is applied from above the pressure tool 921 by a pressing machine or the like.

FIG. 5B is a sectional diagram illustrating a state in which the load 100 is applied by the pressure tool 921.

In a case where the load 100 is applied to the acoustic lens 6 from above by the pressure tool 921, the arms 64a and 64b of the acoustic lens 6 are compressed by being pressed by the pressure tool 921, and compression deformed portions 93a and 93b obtained by compression deforming are generated. That is, a thickness T1 of the arm portions 62a and 62b illustrated in FIG. 5A becomes thin as a thickness T2.

FIG. 5C illustrates a state in which the load 100 is removed and the pressure tool 921 is detached.

Since the pressure tool 921 is detached from the compression deformed portions 93a and 93b, restoring forces 101a and 101b trying to return to the original state are generated. Since an inner surface of the acoustic lens 6 is fixed by the adhesive 7, it is restrained by restraining portions 102a, 102b, and 102c. A part of internal stress of the restoring forces 101a and 101b generated in the arm portions 62a and 62b acts as a force that presses the flexible substrates 435a and 435b against the CMUT chip 2.

The pressing force acts to strengthen the engaging portion between the pad electrodes (21a, 22a and 21b, 22b) of the CMUT chip 2 and the holed-pads 41a and 41b of the flexible substrates 4a and 4b. Accordingly, the flexible substrates 435a and 435b are prevented from being lifted from the CMUT chip 2, and electrical and mechanical connection reliability between the CMUT chip 2 and the flexible substrates 435a and 435b improves.

On the other hand, the arm portions 62a and 62b of the acoustic lens 6 press the connecting portions between the bumps 22a and 22b of the CMUT chip 2 and the holed-pads 41a and 41b of the flexible substrates 435a and 435b. The pressing exerts an operational effect of preventing the flexible substrates 435a and 435b from being lifted from the CMUT chip 2.

Therefore, the pressing effect of the flexible substrates 435a and 435b also occurs even in the flat pad without the holes, rather than the holed-pads 41a and 41b of the flexible substrates 435a and 435b. It is possible to prevent the flexible substrates 435a and 435b from being lifted from the CMUT chip 2.

According to this configuration, in a method of connecting a semiconductor sensor chip, particularly the CMUT chip 2 to an external circuit or the like, that is, in a connecting portion between the pads 21a and 21b of the CMUT chip 2 and pads 21a and 21b (22a and 22b) of the flexible wiring substrates 4a and 4b, it is possible to prevent the lifting of the flexible substrates 435a and 435b from occurring.

Furthermore, since the flexible wiring substrates 435a and 435b are used, cracking at the time of connection between the pads 21a and 21b of the CMUT chip 2 and the pads 21a and 21b (22a and 11b) of the flexible wiring substrates 435a and 435b is prevented from occurring. Accordingly, it is possible to provide a sensor device (ultrasonic probe 1) having enhanced mechanical and electrical connection reliability. Also, it is possible to provide a measuring device using the ultrasonic probe 1, particularly the ultrasonic examination device 8.

Second Embodiment

Figure 6A:
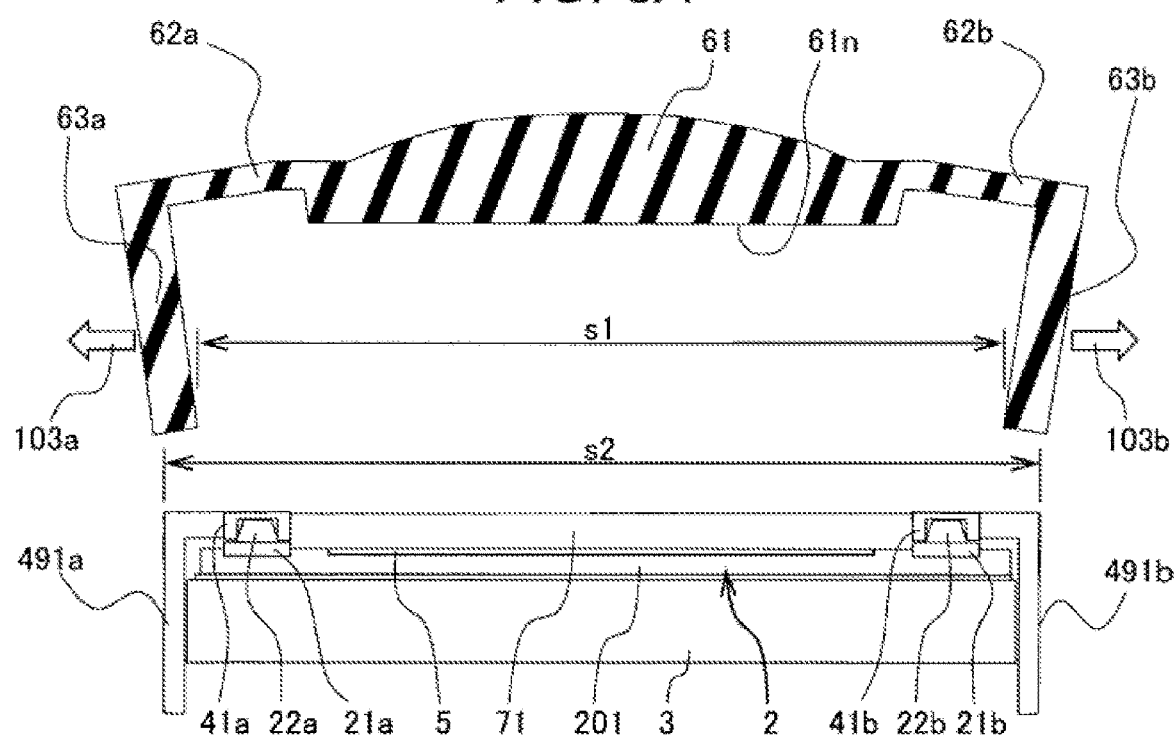
FIG. 6A is a schematic diagram corresponding to a partial section taken along line I-I of FIG. 3, illustrating an installation status of an acoustic lens according to a second embodiment.

FIG. 6A is a schematic diagram corresponding to a partial section taken along line I-I of FIG. 3, illustrating an installation status of an acoustic lens 61 according to a second embodiment.

In the second embodiment, the connection between the CMUT chip 2 and the flexible substrates 491a and 491b is strengthened due to a shape of the acoustic lens 61 without applying a force to the acoustic lens 61.

The acoustic lens 61 of the second embodiment has an arm portion 62a, a frame portion 63a, an arm portion 62b, and a frame portion 63b which are shaped to cover side surfaces of the flexible substrates 491a and 491b.

In the second embodiment, the arm portions 62a and 62b of the acoustic lens 61 are formed in advance in a shape inclined toward the bonding surface of the CMUT chip 2. Therefore, the frame portions 63a and 63b which are continuous respectively to the arm portions 62a and 62b are also inclined toward an inner surface 61n side of the acoustic lens 61. That is, an interval s1 between the frame portion 63a and the frame portion 63b is narrower than an interval s2 between the side surface of the flexible substrate 491a and the side surface of the flexible substrate 491b.

Alternatively, if the frame portions 63a and 63b have the same width relationship as the side surfaces of the flexible substrates 491a and 491b, the frame portions 63a and 63b may be formed into a shape inclined toward the inner surface 61n of the acoustic lens 61. Also, the forming the arm portions 62a and 62b into the inclined shape and the forming the frame portions 63a and 63b into the inclined shape may be performed as follows. A shape curved in a convex shape with respect to the outer surface, that is, a shape having a curvature in a convex shape may also be formed instead of the inclination.

Figure 6B:
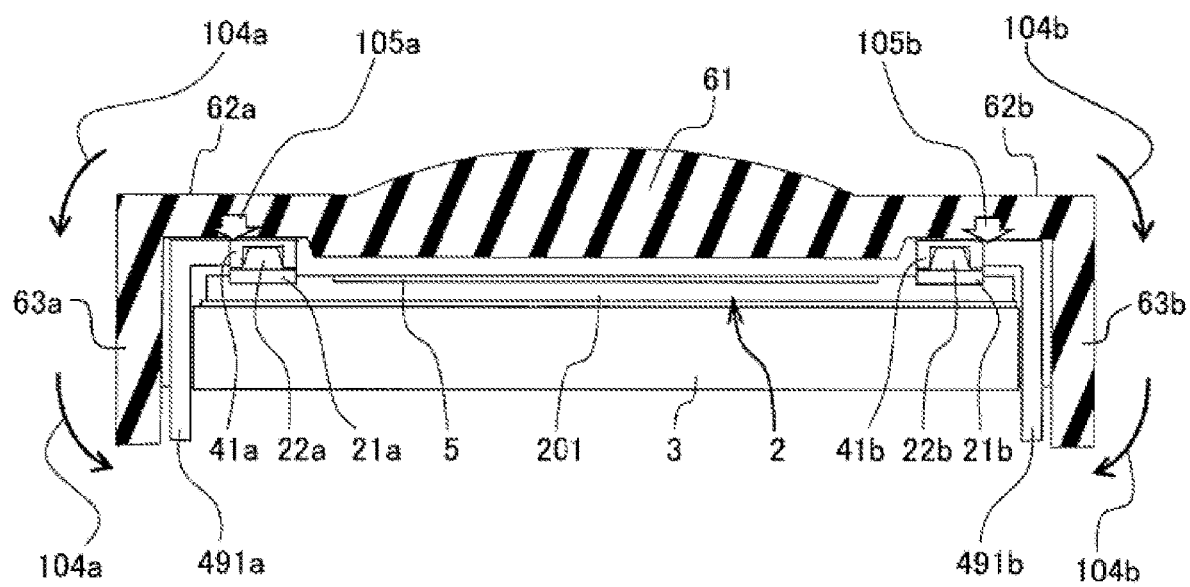
FIG. 6B is a diagram illustrating a state in which an acoustic lens is attached and fixed to an integrated product of a CMUT chip and a flexible substrate.

FIG. 6B illustrates a state in which the acoustic lens 61 is attached and fixed to an integrated product of the CMUT chip 2 and flexible substrates 491a and 491b.

According to the above configuration, the acoustic lens 61 generates restoring forces 104a and 104b which press the flexible substrates 491a and 491b respectively toward insides thereof. The restoring forces 104a and 104b generate pressing forces 105a and 105b that press the flexible substrates 491a and 491b to the CMUT chip 2 side. Accordingly, the bonded portion between the bumps 22a and 22b of the CMUT chip 2 and the holed-pads 41a and 41b of the flexible substrates 491a and 491b is not easily separated, and the flexible substrates 491a and 491b are prevented from being lifted from the CMUT chip 2.

Therefore, the electrical and mechanical connection reliability of the ultrasonic probe 1 (see FIGS. 1 and 3) improves.

Third Embodiment

Figure 7A:
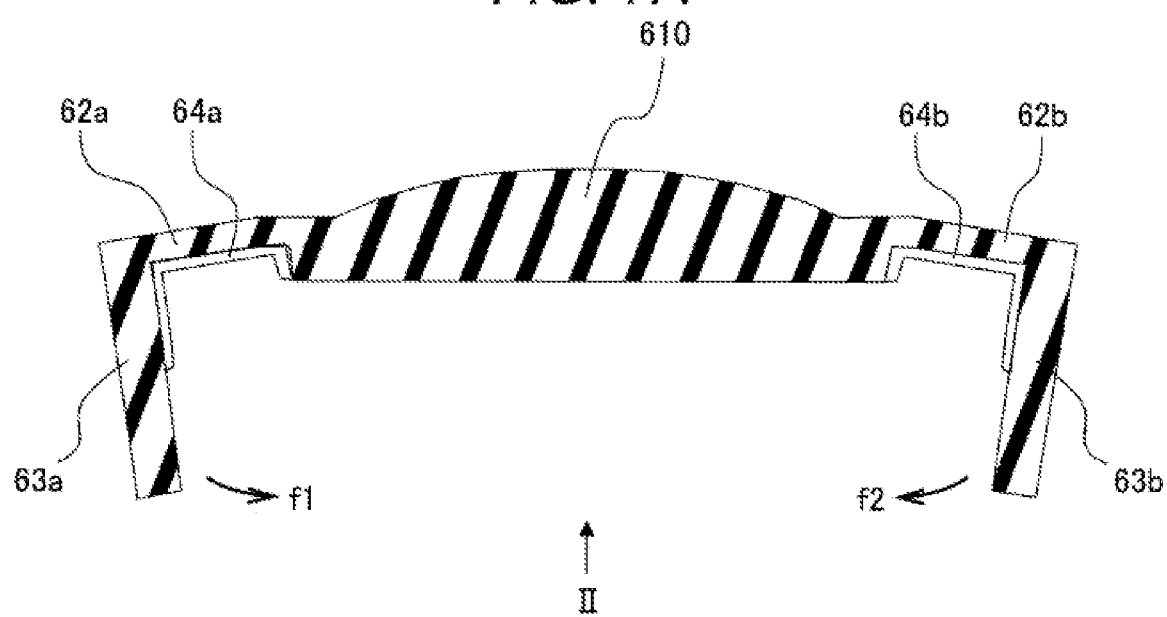
FIG. 7A is a schematic sectional diagram illustrating a structure of an acoustic lens according to a third embodiment.
Figure 7B:
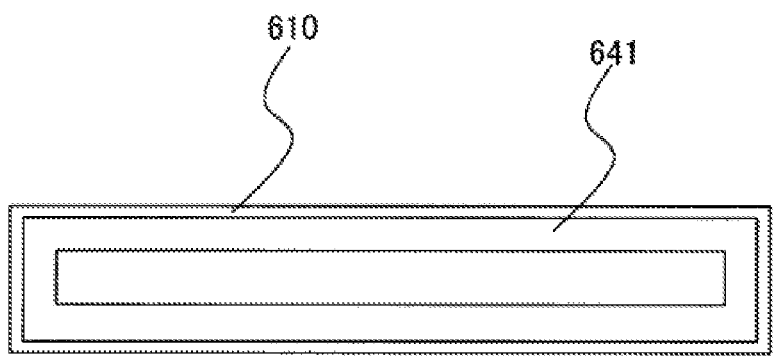
FIG. 7B is a diagram of an inner surface of the acoustic lens viewed from below.

FIG. 7A is a schematic sectional diagram illustrating a structure of an acoustic lens 610 according to a third embodiment. FIG. 7B is a diagram of an inner surface of the acoustic lens 610 viewed from below.

In the acoustic lens 610 according to the third embodiment, the engagement between the bumps 22a and 22b of the CMUT chip 2 and the holed-pads 41a and 41b of the flexible substrates 491a and 491b is strengthened by using the elastic plates 64a and 64b.

In the third embodiment, the elastic plate 64a is provided on an inside of the arm portion 62a and the frame portion 63a of the acoustic lens 610, and the elastic plate 64b is provided on an inside of the arm portion 62b and the frame portion 63b. The elastic plates 64a and 64b have a shape that is inclined toward a side attached to the CMUT chip 2.

As described above, when the acoustic lens 610 is attached and fixed to the assembly of the CMUT chip 2 and the flexible substrates 491a and 491b, the flexible substrates 491a and 491b are pressed against the CMUT chip 2 by restoring forces f1 and f2 of the elastic plates 64a and 64b.

Accordingly, the bumps 22a and 22b of the CMUT chip 2 and the holed-pads 41a and 41b of the flexible substrates 491a and 491b can be firmly engaged. Therefore, the electrical connection reliability of the ultrasonic probe 1 (see FIGS. 1 and 3) improves.

The elastic plates 64a and 64b may have a curved shape or a shape having a curvature in a part, as long as a restoring force is generated after bonding the acoustic lens 610.

FIG. 7B illustrates a case where an elastic plate 641 is an integrated product. However, the elastic plate 641 may not be an integrated product but be a divided product.

When forming the acoustic lens 610, the elastic plates 64a, 64b, and 641 can be formed (insert forming) so as to be integrated with the acoustic lens 610. Also, the elastic plates 64a, 64b, 641, and the acoustic lens 610 can be produced as separate members to be integrated with each other by bonding. Alternatively, there is also an assembly method in which the elastic plates 64a, 64b, and 641 are attached to the assembly of the CMUT chip 2 and the flexible substrates 491a and 491b to generate the pressing force of the flexible substrates 491a and 491b, and then the acoustic lens 610 is mounted thereon. A material of the elastic plates 64a, 64b, and 641 is an elastically deforming material such as an iron alloy, a copper alloy, or stainless steel.

The elastic plates 64a, 64b, and 641 may be made of a deposition film of Cr or the like, and can generate a pressing force to the flexible substrates 491a and 491b using high internal stress.

According to the above configuration, it is possible to prevent the flexible substrates 491a and 491b from being lifted from the CMUT chip 2. Therefore, the electrical and mechanical connection reliability of the ultrasonic probe 1 (see FIGS. 1 and 3) improves.

Fourth Embodiment

Figure 8A:
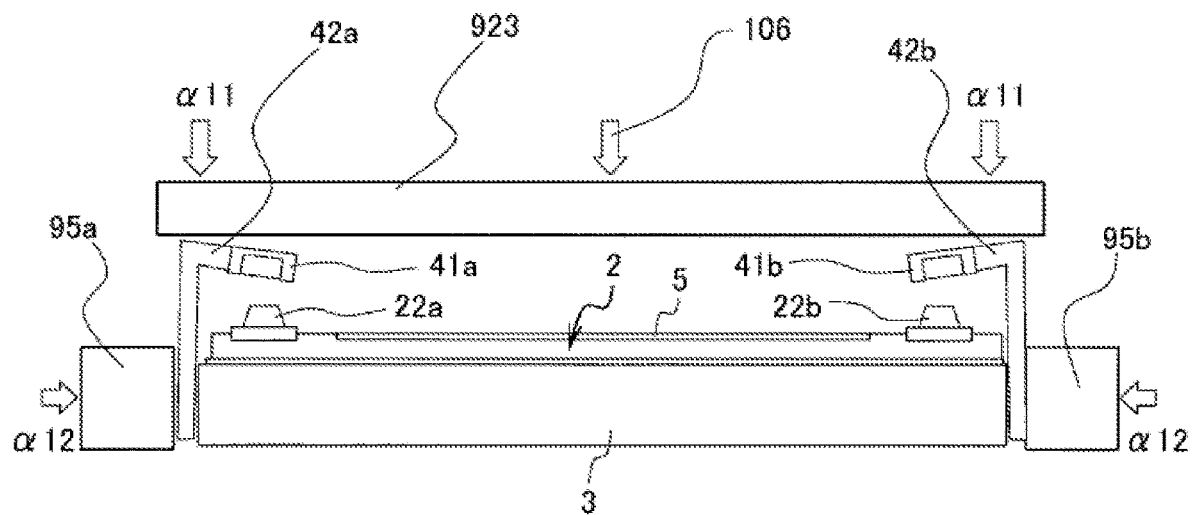
FIG. 8A is a schematic diagram illustrating an installation status of a flexible substrate according to a fourth embodiment.
Figure 8B:
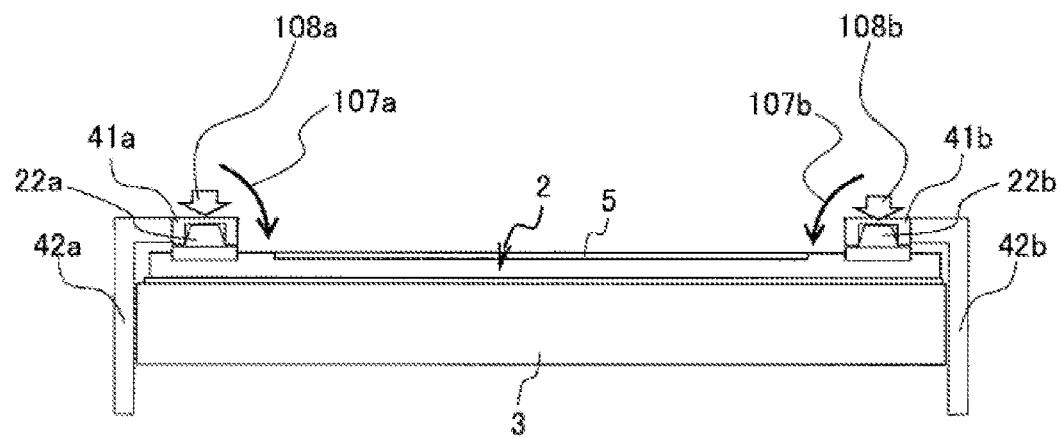
FIG. 8B is a schematic diagram illustrating an installation status of the flexible substrate according to the fourth embodiment.

FIGS. 8A and 8B are schematic diagrams illustrating an installation status of flexible substrates 42a and 42b, according to a fourth embodiment.

As illustrated in FIG. 8A, the holed-pad portions 41a and 41b of the flexible substrates 42a and 42b of the fourth embodiment are bent toward the bumps 22a and 22b of the CMUT chip 2 at an acute angle smaller than 90 degrees.

A load 106 is applied to the flexible substrates 42a and 42b by a pressure tool 923 (arrows all in FIG. 8A), and the holed-pads 41a and 41b of the flexible substrates 42a and 42b are engaged with the bumps 22a and 22b. At this time, fixing tools 95a and 95b hold the flexible substrates 42a and 42b so as to prevent the flexible substrates 42a and 42b from being moved (arrows α12 in FIG. 8A).

When removing the fixing tools 95a and 95b, as illustrated in FIG. 8B, restoring forces 107a and 107b trying to return to the state of FIG. 8A of the flexible substrates 42a and 42b work. The restoring forces 107a and 107b generate pressing forces 108a and 108b by which the holed-pads 41a and 41b are pressed against bumps 22a and 22b of the CMUT chip 2. Accordingly, the flexible substrates 42a and 42b are prevented from being lifted from the CMUT chip 2, and the connections between the holed-pads 41a and 41b of the flexible substrates 42a and 42b and the bumps 22a and 22b of the CMUT chip 2 are strengthened.

As a result, electrical and mechanical connection reliability between the CMUT chip 2 and the flexible substrates 42a and 42b improves.

Fifth Embodiment

Figure 9A:
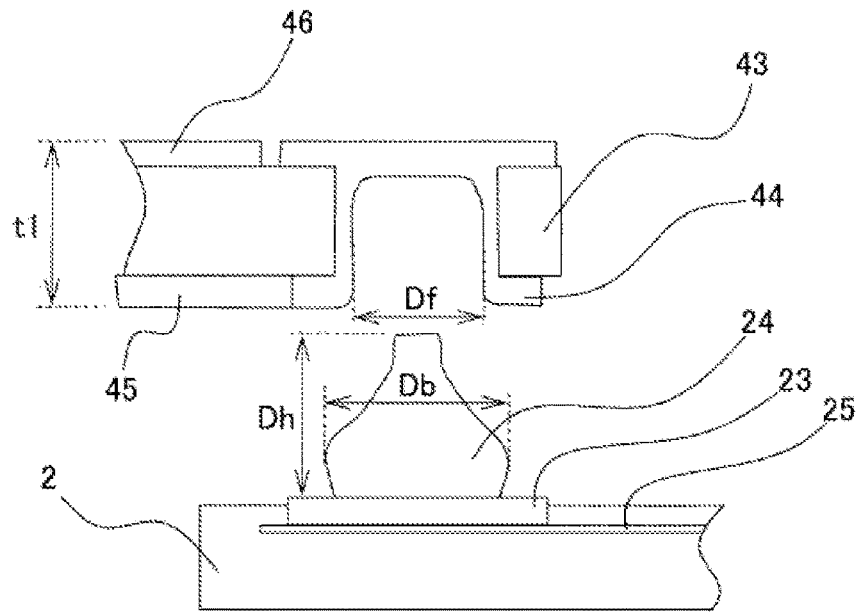
FIG. 9A is a sectional diagram before a connecting portion of a CMUT chip and a holed-pad of a flexible substrate are engaged with each other, according to a fifth embodiment.
Figure 9B:
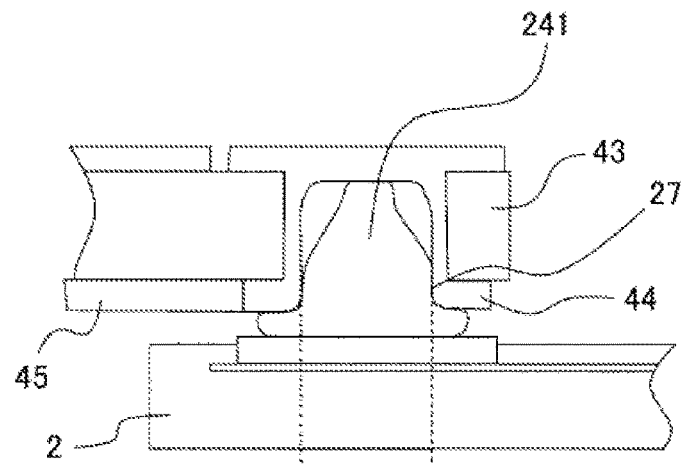
FIG. 9B is a sectional diagram after the holed-pad of the flexible substrate and the bump of the CMUT chip are engaged with each other, according to the fifth embodiment.
Figure 9C:
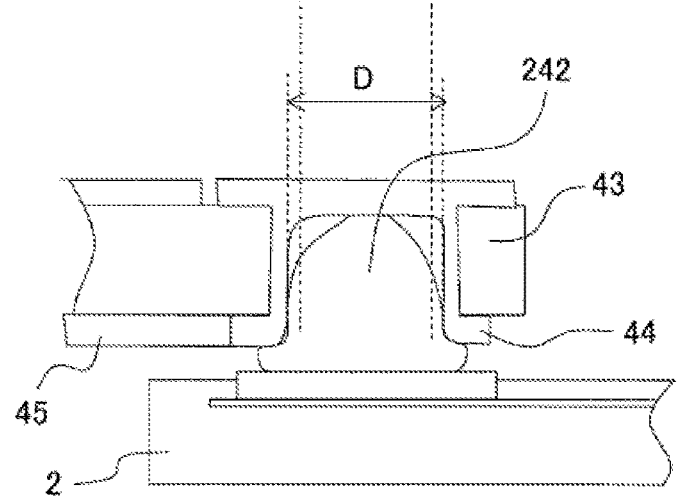
FIG. 9C is a sectional diagram illustrating a case where an outer diameter of the bump is considerably larger than an inner diameter of the holed-pad, according to the fifth embodiment.

FIGS. 9A to 9C are enlarged diagrams illustrating a connecting status between a bump 24 of the CMUT chip 2 and a holed-pad 44 of a flexible substrate 43, according to a fifth embodiment, in the first to fourth embodiments;

The fifth embodiment has a configuration in which the bump 24 of the CMUT chip 2 is fitted or press-fitted to the holed-pad 44 of the flexible substrate 43.

FIG. 9A illustrates a sectional diagram before the bump 24 of the connecting portion of the CMUT chip 2 and the holed-pad 44 of the flexible substrate 43 are engaged with each other, according to the fifth embodiment.

In the CMUT chip 2, an internal wiring 25 of a conductive wire member which connects the element portion 5 (see FIG. 3) and a pad 23 is formed. The bump 24 is formed on the pad 23 of the CMUT chip 2, and the bump 24 is connected to each of predetermined elements (membrane electrodes) (not illustrated) via the internal wiring 25.

On the other hand, the holed-pad 44 is formed on the flexible substrate 43 to which the CMUT chip 2 is electrically connected, and a wiring 45 is connected to the holed-pad 44. The wiring 45 is connected to the circuit boards 97a and 97b via connectors of the flexible substrate 43 (see FIG. 3). A shield wiring 46 is formed on a back surface of the flexible substrate 43. A portion having a maximum outer diameter Db of the bump 24 of the CMUT chip 2 is larger than an inner diameter Df of the holed-pad of the flexible substrate 43 (Db>Df). It is preferable to have a dimension to extent that each side surface slides thereof when engaged with the bump 24.

FIG. 9B illustrates a sectional diagram after the holed-pad 44 of the flexible substrate 43 and a bump 241 of the CMUT chip 2 are engaged with each other, according to the fifth embodiment.

The holed-pad 44 of the flexible substrate 43 is formed to have a diameter smaller than that of the bump 241 of the CMUT chip 2.

Therefore, the bump 241 of the CMUT chip 2 is press-fitted into the holed-pad 44 of the flexible substrate 43 to be plastically deformed. In this case, an outer periphery of the bump 241 of the CMUT chip 2 and an inner periphery of the holed-pad 44 of the flexible substrate 43 slide on a sliding surface 27.

The bump 241 or a surface oxide film of the holed-pad 44 is scraped off due to the sliding. Sufficient electric connection between the bump 241 and the holed-pad 44 is obtained. Further, mechanical strength also increases.

Accordingly, connection reliability between the bump 241 of the CMUT chip 2 and the holed-pad 44 of the flexible substrate 43 improves.

As illustrated in FIGS. 9A and 9B, since the bump 24 (241) and the holed-pad 44 are press-fitted to and engaged with each other, it is not required to perform heating unlike the wire bonding or connection using solder. Therefore, it is even applicable to a case where heat resistant temperature of necessary members such as the backing material or an adhesive sheet is low. Regarding material selection, it is possible to select a preferable material for acoustic characteristics of the ultrasonic waves.

The wiring 45 of the flexible substrate 43 can be formed simultaneously with the holed-pad 44 by plating or the like.

FIG. 9C illustrates a case where an outer diameter D of a bump 242 is considerably larger than an inner diameter of the holed-pad 44, according to the fifth embodiment.

Since the flexible substrate 43 is a resin such as polyimide, even if a hole of the holed-pad 44 formed in the flexible substrate 43 is expanded, it is elastically deformed. Therefore, cracks or fractures do not occur in the flexible substrate 43, and the electrical and mechanical connection reliability between the bump 242 of the CMUT chip 2 and the holed-pad 44 of the flexible substrate 43 improves.

On the contrary to the first to fifth embodiments, in a case where a substrate on which the holed-pad 44 is formed is a brittle material such as semiconductor silicon, the hole of the holed-pad 44 is pressed and widened, and thus the fractures may occur.

On the other hand, in an assembly (see FIGS. 3 to 6B, FIGS. 8A to 9B) including the CMUT chip 2, the backing material 3, and the flexible substrates 4a to 43 according to the first to fifth embodiments, when an environmental temperature changes, since a coefficient of thermal expansion of the silicone which is a base material of the CMUT chip 2 (approximately 2.6 ppm/° C.) and a coefficient of thermal expansion of the flexible substrates 4a to 43 (approximately 10 to 30 ppm/° C.) are different from each other, thermal stress is generated.

However, the Young's modulus of the flexible substrates 4a to 43 is approximately 3 to 10 GPa, which is considerably smaller than the Young's modulus of the silicone of the base material of the CMUT chip 2 (approximately 190 GPa) and is easy to deform flexibly. Therefore, a force enough to peel off the engaging portion between the bumps 22a, 22b, and 24 of the CMUT chip 2 and the holed-pads 41a, 41b, and 44 of the flexible substrates 4a to 43. Therefore, the flexible substrates 4a to 43 are prevented from being lifted from the CMUT chip 2, and electrical and mechanical connection reliability between the bumps 22a, 22b, and 24 of the CMUT chip 2 and the holed-pads 41a, 41b, and 44 of the flexible substrates 4a to 43 improves.

As illustrated in FIGS. 9A to 9C, in a step of press-fitting and engaging the bump 24 (241 and 242) and the holed-pad 44 with each other, even when heating is performed at a temperature equal to or lower than the heat resistance temperature of constitution materials such as the backing material 3, the adhesive sheet, or the adhesive 7 (FIGS. 4 to 5C), it is easy to deform the bump 24 of the CMUT chip 2 or deform the holed-pad 44 of the flexible substrate 43 at the time of engaging.

Accordingly, electrical and mechanical bonding between the bump 24 of the CMUT chip 2 and the holed-pad 44 of the flexible substrate 43 becomes favorable. Also, ultrasonic waves are applied when engaging the bump 24 and the holed-pad 44 with each other, the sliding surfaces are easy to bond to each other.

In FIG. 9A, when the diameter Db of the bump 24 is, for example, 100 μm, a height Dh of the bump 24 is preferably 50 μm to 200 μm, which is 0.5 to 2 times the height. Since a thickness of the acoustic lens 6 can be reduced, it is preferable that a thickness t1 of the flexible substrate 43 has small protrusion from an ultrasonic transmitting and receiving surface of the element portion 5 (see FIGS. 3 and 4). For example, when the thickness of the flexible substrate 43 is set to 15 μm, a bump height may be set to 15 μm and a bump diameter may be set to 7.5 to 30 μm from the relationship between the diameter Db and the height Dh of the bump 24. Further, a gap between the flexible substrate 43 and the CMUT chip 2 may be filled with a resin material such as underfill. In this case, the filled resin material is made not to spread to the element portion 5.

Figure 10A:
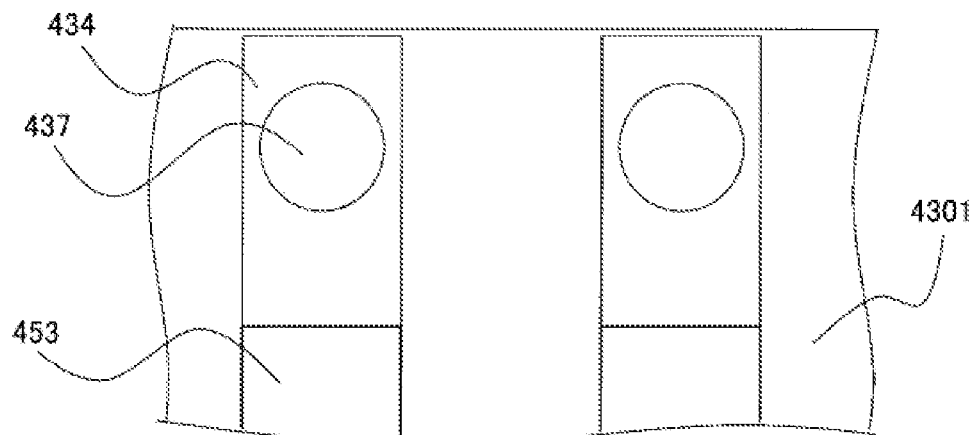
FIG. 10A is a schematic diagram illustrating a shape of the holed-pad of the flexible substrate according to the fifth embodiment.
Figure 10B:
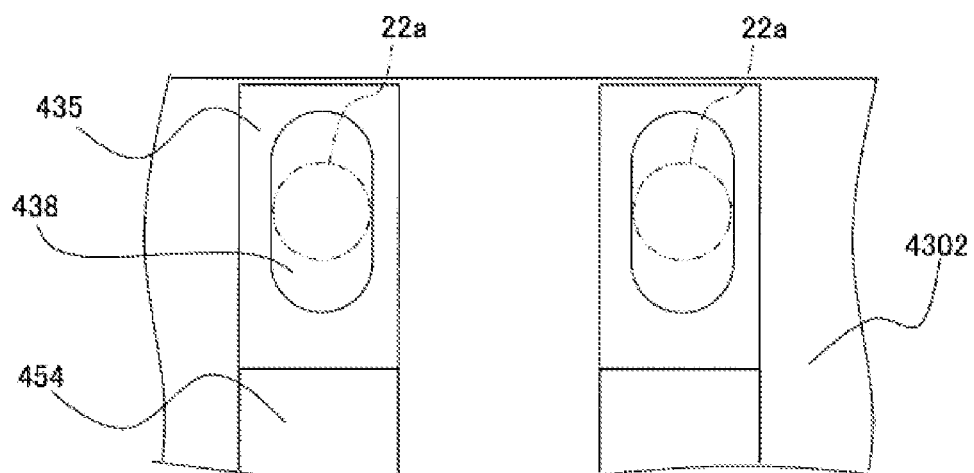
FIG. 10B is a schematic diagram illustrating a shape of the holed-pad of the flexible substrate according to the fifth embodiment.
Figure 10C:
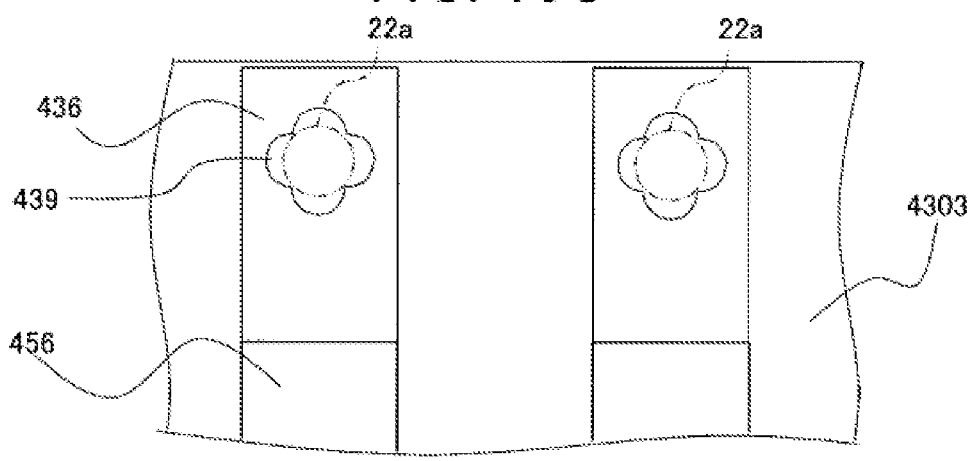
FIG. 10C is a schematic diagram illustrating a shape of the holed-pad of the flexible substrate according to the fifth embodiment.

FIGS. 10A to 10C are schematic diagrams illustrating shapes of holed-pads 434 to 436 of flexible substrate 4301 to 4303 according to the fifth embodiment.

FIGS. 10A to 10C illustrate respectively two pieces of each of the holed-pads 434 to 436, as an example.

FIG. 10A illustrates a case where a hole 437 of the holed-pad 434 of the flexible substrate 4301 of the fifth embodiment is circular. The hole 437 is formed by a laser drill or the like.

FIG. 10B illustrates a case where a hole 438 of the holed-pad 435 of the flexible substrate 4302 of the fifth embodiment is a long round hole. The bump 22a of the CMUT chip 2 to be engaged with the hole 438 is indicated by a two-dot chain line.

The hole 438 in the holed-pad 435 can also be formed with the laser drill.

Since the hole 438 of the holed-pad 435 of the flexible substrate 4302 is the long round hole, even if the bump 22a of the CMUT chip 2 is shifted in a longitudinal direction thereof, it can be press-fitted thereto. The hole 438 may be a long hole other than the long round hole.

FIG. 10C illustrates a variant case where a hole 439 of the holed-pad 436 of the flexible substrate 4303 of the fifth embodiment is formed of a plurality of arcs e1 to e4. The bump 22a of the CMUT chip 2 is indicated by a two-dot chain line.

The hole 439 can be formed by, for example, overlapping four laser spots.

Since the hole 439 of the holed-pad 436 is formed of the plurality of the arcs e1 to e4, even when the bump 22a of the CMUT chip 2 is shifted somewhat in two directions, it can be press-fitted thereto.

In a case where the shapes of the holes 438 and 439 illustrated in FIGS. 10B and 10C, a gap between the bump 22a and the holes 438 and 439 can be formed even after the bump 22a of the CMUT chip 2 is press-fitted to be engaged therewith. Therefore, an inside of the holes 438 and 439 into which the bumps 22a are inserted is not blocked, and there is an effect that condensation is suppressed.

Also, even when the engaging portion between the bump 22a and the holes 438 and 439 is filled with resin or the like, if a gap (see FIGS. 10B and 10C) is provided between the bump 22a and the holes 438 and 439, the resin penetrates into the inside of the holes 438 and 439. Therefore, it is possible to achieve more firm fixing.

Sixth Embodiment

Figure 11:
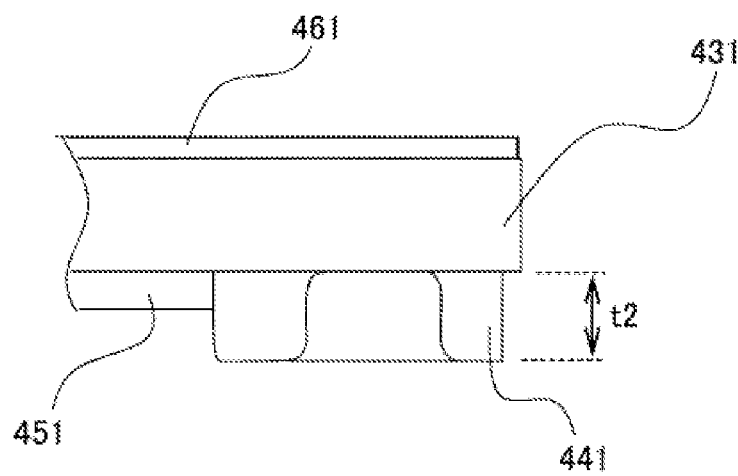
FIG. 11 is an enlarged diagram illustrating a portion in the vicinity of a holed-pad of a flexible substrate according to a sixth embodiment.

FIG. 11 is an enlarged diagram illustrating a portion in the vicinity of a holed-pad 441 of a flexible substrate 431 according to a sixth embodiment.

In the sixth embodiment, the holed-pad 441 is formed on a surface of the flexible substrate 431, and the flexible substrate 431 has no hole.

A wiring 451 is connected to the holed-pad 441. A shield 461 responsible for insulation is formed on a back surface of the flexible substrate 431.

Since a step of forming a hole in the flexible substrate 431 can be omitted, the manufacturing costs are reduced. However, a thickness of the engaging portion of the flexible substrate 431 increases by a thickness t2 of the holed-pad 441.

Seventh Embodiment

Figure 12:
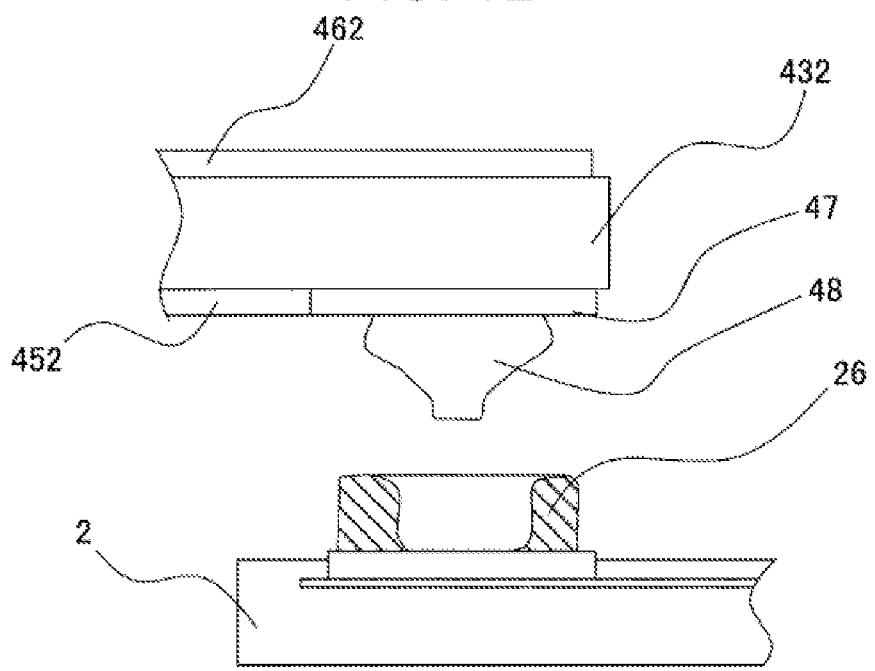
FIG. 12 is a partial enlarged sectional diagram illustrating a shape of a bump electrode of a flexible substrate and a pad of a CMUT chip according to a seventh embodiment.

FIG. 12 is a partial enlarged sectional diagram illustrating a shape of an electrode of a bump 48 of a flexible substrate 432 and a holed-pad 26 of the CMUT chip 2 according to a seventh embodiment.

The seventh embodiment has a configuration in which the bump 48 is formed in a pad 47 of the flexible substrate 432 and the holed-pad 26 is formed in the pad of the CMUT chip 2.

Regarding an engaging state between the bump 48 of the flexible substrate 432 and the holed-pad 26 of the CMUT chip 2, the configuration described in FIGS. 9A to 9C can be applied, and the same operational effects are obtained.

Eighth Embodiment

Figure 13A:
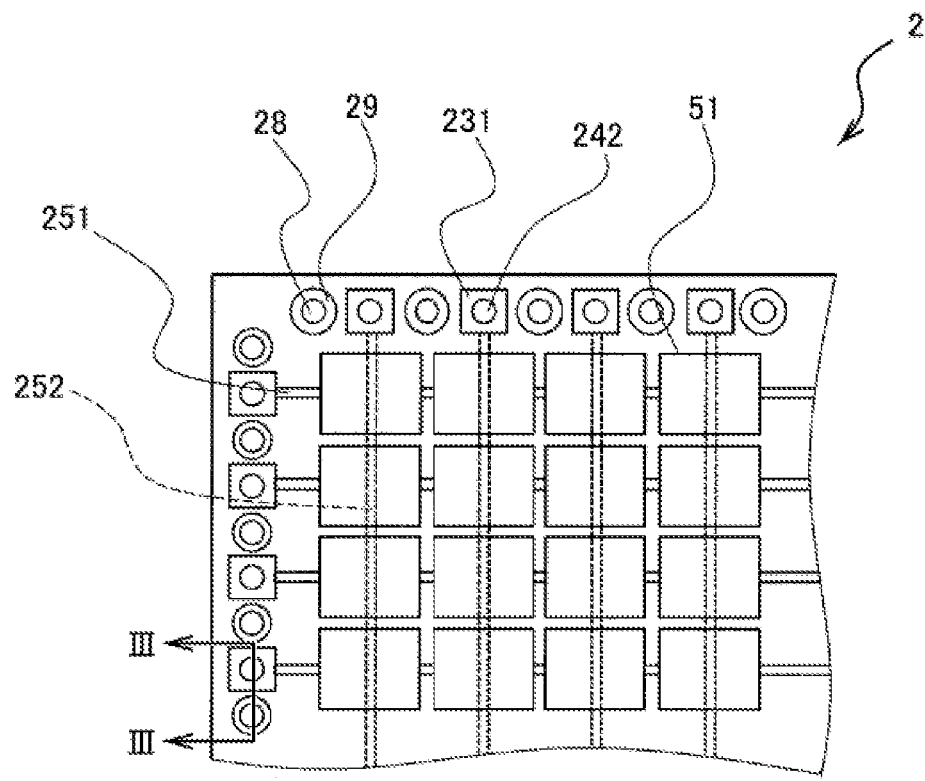
FIG. 13A is a diagram illustrating an example of a top view of a CMUT chip according to an eighth embodiment.
Figure 13B:
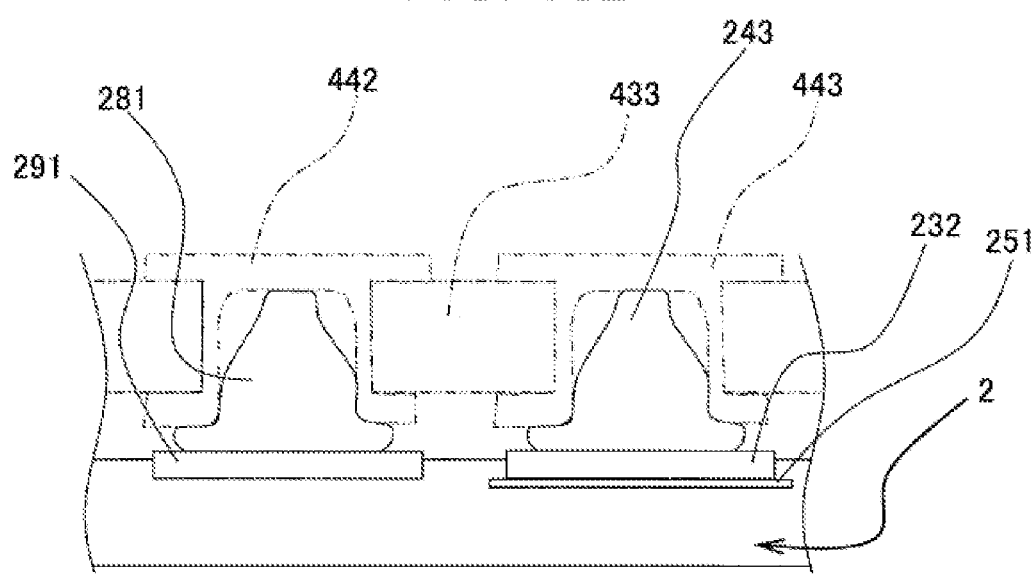
FIG. 13B is a diagram illustrating an example of a section taken along a line III-III of FIG. 13A in a state of adding a flexible substrate, according to the eighth embodiment.

FIGS. 13A and 13B illustrate the CMUT chip 2 in which dummy electrodes are arranged, according to an eighth embodiment. FIG. 13A illustrates an example of a top view of the CMUT chip 2 of the eighth embodiment. FIG. 13B illustrates an example of a section taken along a line III-III of FIG. 13A in a state of adding a flexible substrate 433 (indicated by a two-dot chain line), according to the eighth embodiment.

In the CMUT chip 2 of the eighth embodiment, dummy electrodes are arranged, and the joining between the CMUT chip 2 and the flexible substrate 433 (indicated by a two-dot chain line) is enhanced.

Internal wirings 251 and 252 are connected to an element 51 configured of a plurality of diaphragm arrays (not illustrated) (a row of membrane electrodes and fixed electrodes) in the CMUT chip 2 of FIG. 13A. The bump 242 is formed on a pad 231 of the CMUT chip 2, and the element 51 is connected thereto by the internal wirings 251 and 252. A dummy bump 28 is formed on a dummy pad 29 of the CMUT chip 2.

As illustrated in FIG. 13B which is a sectional view taken along a line III-III of FIG. 13A, the internal wiring 251 is connected to a pad 232 that is connected to the element 51. An internal wiring is not connected to a dummy pad 291. According to the connection by a dummy bump 281, the number of engaging positions between the CMUT chip 2 and a holed-pad 442 of a flexible substrate 433 increases, and the mechanical strength of the connection increases. Accordingly, the mechanical connection reliability between the flexible substrate 433 and the CMUT chip 2 can improve.

Ninth Embodiment

Figure 14:
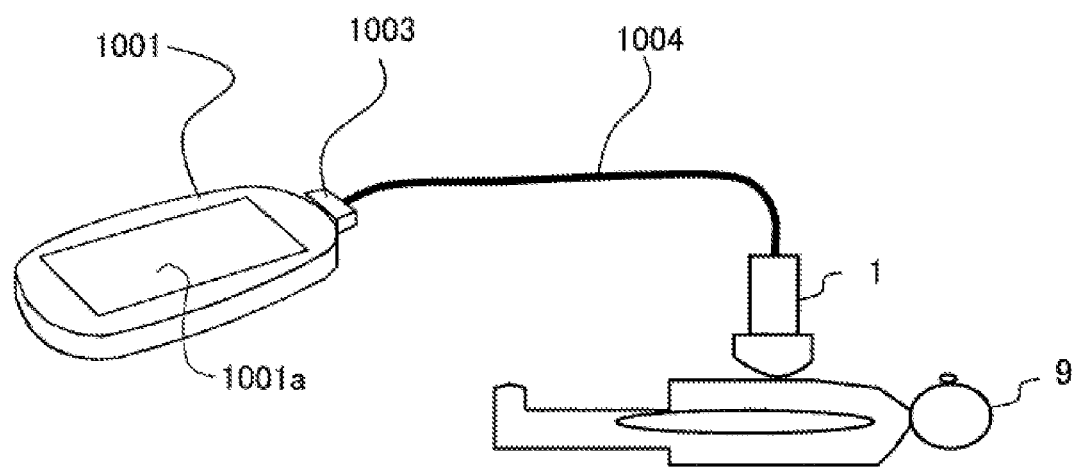
FIG. 14 is an external schematic diagram illustrating a configuration in which an ultrasonic probe is connected to a smartphone to perform an ultrasonic examination of an object, according to a ninth embodiment.

FIG. 14 illustrates an external schematic diagram illustrating a configuration in which the ultrasonic probe 1 is connected to a smartphone 1001 to perform an ultrasonic examination of the object 9, according to a ninth embodiment.

The ninth embodiment has a configuration in which the ultrasonic probe 1 is connected to the smartphone 1001.

A connector 1003 for connecting to an external connection connector (not illustrated) is attached to the smartphone 1001 of the ninth embodiment. A tip of a cable 1004 connected to the ultrasonic probe 1 is connected to the connector 1003.

In the smartphone 1001, an application software having a function of transmitting and receiving ultrasonic waves from the ultrasonic probe 1 (transmitting function and receiving function), and a function of converting a signal received by the ultrasonic probe 1 into an image and displaying the image is installed. In the application software, a mode for transmission or reception of the ultrasonic waves is controlled appropriately, and an ultrasonic image is displayed on a screen 1001a of the smartphone 1001.

In addition, the smartphone 1001 can send acquired image information to a medical examination system cloud server and the like using wireless or wired communication, and can conduct accurate examination and diagnosis using artificial intelligence such as machine learning. Also, when findings of disease are obtained by examination or the like, information such as a treatment method or effective medication can be drawn from the artificial intelligence.

Tenth Embodiment

Figure 15:
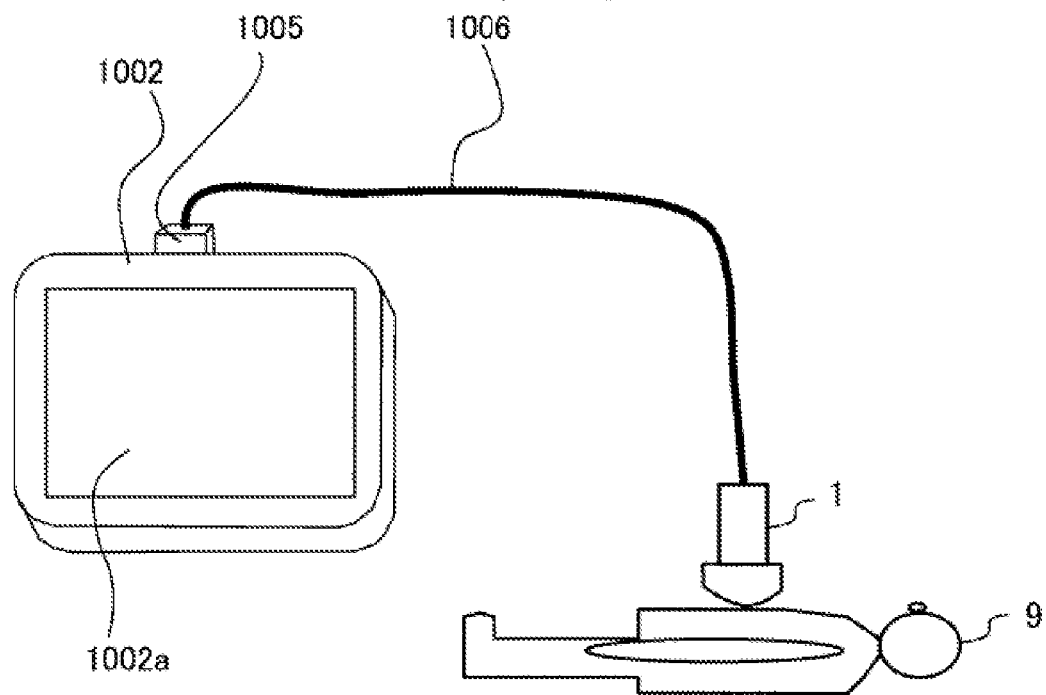
FIG. 15 is an external diagram of a configuration in which an ultrasonic probe is connected to a tablet terminal to perform an ultrasonic examination of an object, according to a tenth embodiment.

FIG. 15 illustrates an external diagram illustrating a configuration in which the ultrasonic probe 1 is connected to a tablet terminal 1002 to perform an ultrasonic examination of the object 9, according to a tenth embodiment.

The tenth embodiment has a configuration in which the ultrasonic probe 1 is connected to the tablet terminal 1002.

A connector 1005 for connecting to an external connection connector (not illustrated) is attached to the tablet terminal 1002 of the tenth embodiment. A tip of a cable 1006 connected to the ultrasonic probe 1 is connected to the connector 1005.

In the tablet terminal 1002, an application software having a function of transmitting and receiving ultrasonic waves from the ultrasonic probe 1 (transmitting function and receiving function), and a function of converting a signal received by the ultrasonic probe 1 into an image (image forming unit) and displaying the image is installed. Accordingly, the ultrasonic image is displayed on a screen 1002a of the tablet terminal 1002.

Examination support using the application software or the artificial intelligence, utilization of the cloud server, and the like are the same as those of the ultrasonic examination using the smartphone 1001 illustrated in FIG. 14 of the ninth embodiment.

Eleventh Embodiment

FIGS. 16A to 16F are sectional diagrams illustrating steps for forming the holed-pad 44 (see FIG. 9) (holed-pads 41a and 41b of FIG. 4) formed in the flexible substrate 43, according to an eleventh embodiment.

The eleventh embodiment illustrates an example of steps of forming the holed-pad 44 in the flexible substrate 43.

Hereinafter, the steps of forming the holed-pad 44 will be sequentially described.

Figure 16A:
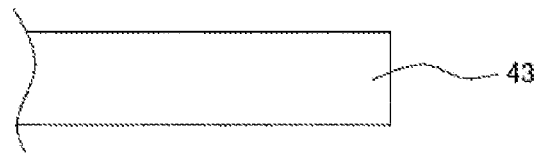
FIG. 16A is a sectional diagram illustrating a step for forming a holed-pad formed in a flexible substrate, according to an eleventh embodiment.
Figure 16B:
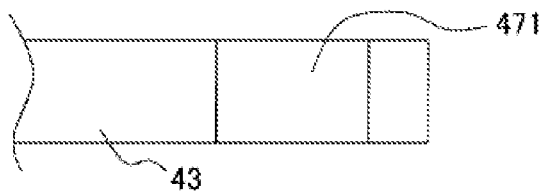
FIG. 16B is a sectional diagram illustrating a step for forming the holed-pad formed in the flexible substrate, according to the eleventh embodiment.

As illustrated in FIG. 16B, a through hole 471 is formed in the unprocessed flexible substrate 43 illustrated in FIG. 16A by a laser processing machine.

Figure 16C:
FIG. 16C is a sectional diagram illustrating a step for forming the holed-pad formed in the flexible substrate, according to the eleventh embodiment.

Subsequently, as illustrated in FIG. 16C, a film 472 is stretched over one side of the flexible substrate 43 in which the through hole 471 is formed.

Figure 16D:
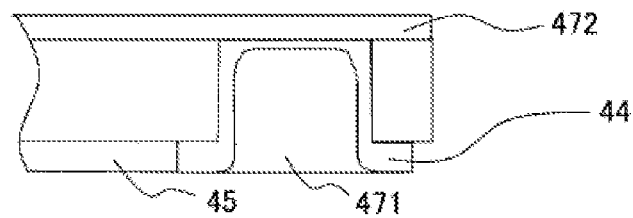
FIG. 16D is a sectional diagram illustrating a step for forming the holed-pad formed in the flexible substrate, according to the eleventh embodiment.
Figure 16E:
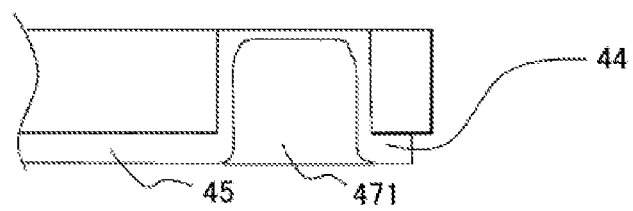
FIG. 16E is a sectional diagram illustrating a step for forming the holed-pad formed in the flexible substrate, according to the eleventh embodiment.

Subsequently, as illustrated in FIG. 16D, the holed-pad 44 and the wiring 45 are formed by sputtering or plating method, and as illustrated in FIG. 16E, the film 472 is removed.

Figure 16F:
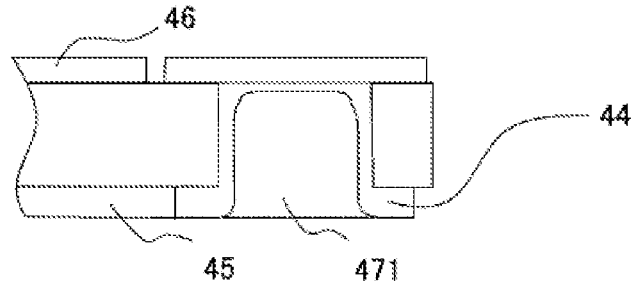
FIG. 16F is a sectional diagram illustrating a step for forming the holed-pad formed in the flexible substrate, according to the eleventh embodiment.

Then, as illustrated in FIG. 16F, a shield wiring 45 or the like is formed on a surface on a side opposite the holed-pad 46.

Twelfth Embodiment

FIGS. 17A to 17D are diagrams illustrating steps of forming the holed-pad 441 illustrated in FIG. 11, according to a twelfth embodiment.

The twelfth embodiment illustrates an example of steps of forming the holed-pad 441 in the flexible substrate 431.

Hereinafter, the steps of forming the holed-pad 441 will be sequentially described.

Figure 17A:
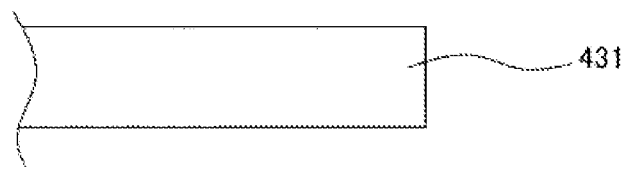
FIG. 17A is a diagram illustrating a step of forming the holed-pad illustrated in FIG. 11, according to a twelfth embodiment.
Figure 17B:
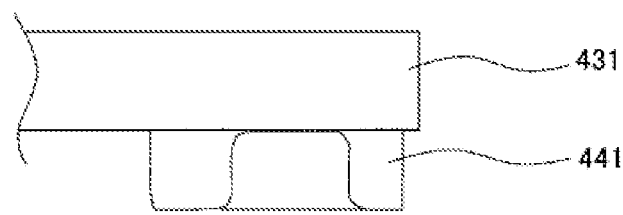
FIG. 17B is a diagram illustrating a step of forming the holed-pad illustrated in FIG. 11, according to the twelfth embodiment.

As illustrated in FIG. 17B, the holed-pad 441 is formed in the unprocessed flexible substrate 431 illustrated in FIG. 17A by a sputtering or plating method.

Figure 17C:
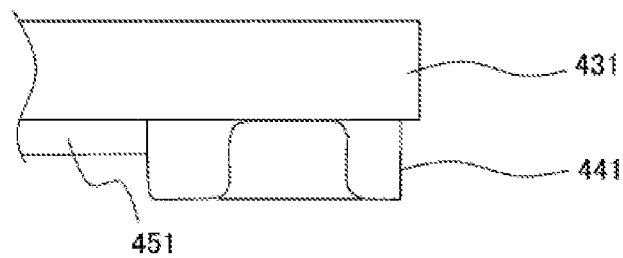
FIG. 17C is a diagram illustrating a step of forming the holed-pad illustrated in FIG. 11, according to the twelfth embodiment.

Next, as illustrated in FIG. 17C, the wiring 451 connected to the holed-pad 441 is formed by sputtering or plating in the same manner.

Figure 17D:
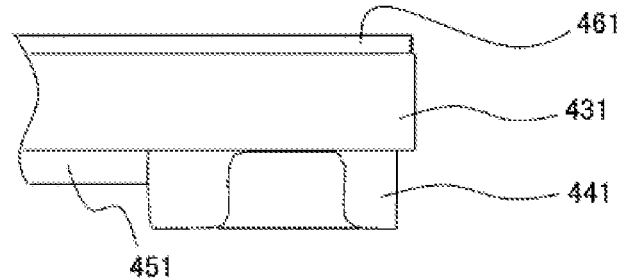
FIG. 17D is a diagram illustrating a step of forming the holed-pad illustrated in FIG. 11, according to the twelfth embodiment.

Then, as illustrated in FIG. 17D, the shield wiring 461 is formed on a surface on a side opposite the holed-pad 441.

In a case where the holed-pad 441 is formed in this step, the forming steps illustrated in FIGS. 16A to 16F, that is, a step of laser drilling (FIG. 16B) or attaching the film 472 (FIG. 16C) can be omitted. Therefore, it is possible to reduce manufacturing costs by reducing steps.

However, there is a disadvantage that the holed-pad 441 protrudes from the surface of the flexible substrate 431 and the thickness contributing to the connection increases. Therefore, in a case of reducing the thickness of the connecting portion between the CMUT chip 2 and the flexible substrate 431 as much as possible, it is preferable that the holed-pad 44 is formed in the steps illustrated in FIG. 16A to FIG. 16F.

As described in the above, the ultrasonic examination device (FIGS. 1 and 2) includes the transmitting function (82) that transmits the ultrasonic waves, the receiving function (82) that receives the received signal of the ultrasonic waves reflected from the object 9, the image forming unit (83) that converts the received signal into an image, the display unit 85 that displays the image, and the ultrasonic probe 1, thereby obtaining the ultrasonic examination device 8 having the ultrasonic probe 1 exhibiting the described operational effects.

Accordingly, it is possible to provide the ultrasonic probe 1 having improved reliability of the external electrode connecting portion of an ultrasonic sensor and the ultrasonic examination device 8 including the same.

Other Embodiments

1. In each embodiment, a pad, a bump, or a wiring (a conductive wire member) indicates what is considered to be necessary for explanation, and does not necessarily showing all the pad, the bump, or the wiring (conductive wire member) for the configuration. Practically, it can be considered that almost all the configurations are mutually connected.

2. The number of the bumps or the pads formed in the CMUT chip 2 of the embodiment is not limited to the illustration. Any number of bumps or the pads may be disposed according to a size or disassemble ability of the ultrasonic element 1.

3. The present invention is not limited to the above described embodiments, and includes various modification examples. For example, the above embodiments have been described in detail in order to explain the present invention in an easy-to-understand manner, and are not necessarily limited to those having all the described configurations. It is also possible to replace a part of the configuration of a certain embodiment with the configuration of another embodiment, and it is also possible to add a configuration of a certain embodiment to the configuration of another embodiment. In addition, it is also possible to add, delete, or replace another configuration with respect to a part of the configuration of each embodiment.

What is claimed is:

1. An ultrasonic probe comprising:
an oscillator;
a base on which the oscillator is provided;
a base conductive wire portion connected to the oscillator;
a bump electrode portion formed on a flexible substrate and not provided on a side of the base on which the oscillator is provided and supplying a signal to the oscillator via the base conductive wire portion;
a concave holed-pad portion engaging directly with the bump electrode portion by receiving the bump electrode portion within the concave holed-pad portion, wherein
the concave holed-pad portion is formed on the side of the base on which the oscillator is provided; and
an acoustic lens provided such that a force toward the bump electrode portion is applied to the concave holed-pad portion.

2. The ultrasonic probe according to claim 1, wherein
an arm portion provided on a periphery of a curved surface portion of the acoustic lens is formed so as to apply an inward force toward an inner surface of the acoustic lens.

3. The ultrasonic probe according to claim 1, further comprising:
an elastic plate provided on an inner side of an arm portion provided on a periphery of a curved surface portion of the acoustic lens.

4. The ultrasonic probe according to claim 1, further comprising:
a dummy pad; and
a dummy bump, wherein
the dummy pad and the dummy bump are engaged with each other.

5. The ultrasonic probe according to claim 1, wherein
in the concave holed-pad portion, an upper surface shape of a hole into which the bump electrode portion is press-fitted is a slot.

6. The ultrasonic probe according to claim 1, wherein
in the concave holed-pad portion, an upper surface shape of a hole into which the bump electrode portion is press-fitted has a plurality of circular arcs.

7. The ultrasonic probe according to claim 1, wherein
the bump electrode portion and the flexible substrate are disposed on the oscillator when the concave holed-pad portion is engaged with the bump electrode portion.

8. The ultrasonic probe according to claim 1, wherein
the bump electrode portion is plastically deformed by the concave holed-pad portion.

9. The ultrasonic probe according to claim 1, wherein
the concave holed-pad portion is elastically expanded by the bump electrode portion.

10. An ultrasonic examination device having a transmitting function of ultrasonic waves and a receiving function of ultrasonic waves reflected from an object, the device comprising:
    an image forming unit converting a received signal obtained from the receiving function into an image;
    a display unit displaying the image; and
    the ultrasonic probe according to claim 1.

11. A smartphone having a transmitting function of ultrasonic waves and a receiving function of ultrasonic waves reflected from an object, the smartphone comprising:
    an image forming unit converting a received signal obtained from the receiving function into an image;
    a display unit displaying the image; and
    the ultrasonic probe according to claim 1.

12. A tablet having a transmitting function of ultrasonic waves and a receiving function of ultrasonic waves reflected from an object, the tablet comprising:
    an image forming unit converting a received signal obtained from the receiving function into an image;
    a display unit displaying the image; and
    the ultrasonic probe according to claim 1.

13. An ultrasonic probe comprising:
    an acoustic lens;
    an oscillator;
    a base on which the oscillator is provided;
    a base conductive wire portion connected to the oscillator;
    a bump electrode portion formed on a flexible substrate and not provided on a side of the base on which the oscillator is provided and supplying a signal to the oscillator via the base conductive wire portion; and
    a concave holed-pad portion to which the bump electrode portion is press-fitted by receiving the bump electrode portion within the concave holed-pad portion, wherein the concave holed-pad portion is formed on the side of the base on which the oscillator is provided.

14. An ultrasonic probe comprising:
    an acoustic lens;
    an oscillator;
    a base on which the oscillator is provided;
    a base conductive wire portion connected to the oscillator;
    a bump electrode portion formed on a flexible substrate and not provided on a side of the base on which the oscillator is provided and supplying a signal to the oscillator via the base conductive wire portion; and
    a concave holed-pad portion facing the bump electrode portion and connected thereto by receiving the bump electrode portion within the concave holed-pad portion, wherein
    the concave holed-pad portion is formed on the side of the base on which the oscillator is provided.

\* \* \* \* \*